US008754230B2

(12) United States Patent
Livingston et al.

(10) Patent No.: US 8,754,230 B2
(45) Date of Patent: Jun. 17, 2014

(54) 4-PYRIDINONE COMPOUNDS AND THEIR USE FOR CANCER

(71) Applicant: Bristol-Myers Squibb Company, Princeton, NJ (US)

(72) Inventors: Robert C. Livingston, Burlingame, CA (US); William P. Gallagher, Princeton, NJ (US); Robert M. Borzilleri, New Hope, PA (US); Zhen-Wei Cai, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/026,628

(22) Filed: Sep. 13, 2013

(65) Prior Publication Data

US 2014/0012007 A1 Jan. 9, 2014

Related U.S. Application Data

(62) Division of application No. 12/863,713, filed as application No. PCT/US2009/031665 on Jan. 22, 2009, now Pat. No. 8,558,000.

(60) Provisional application No. 61/121,931, filed on Dec. 12, 2008, provisional application No. 61/022,848, filed on Jan. 23, 2008.

(51) Int. Cl.
*C07D 211/72* (2006.01)
*C07D 213/74* (2006.01)

(52) U.S. Cl.
CPC .................................. *C07D 213/74* (2013.01)
USPC ......................................................... 546/290

(58) Field of Classification Search
CPC ........................................................ C07D 213/74
See application file for complete search history.

(56) References Cited

U.S. PATENT DOCUMENTS

| | | | |
|---|---|---|---|
| 3,646,202 A | 2/1972 | Mrozik | |
| 4,547,218 A | 10/1985 | Malhotra et al. | |
| 5,132,428 A | 7/1992 | Von Oppolzer | |
| 6,057,336 A | 5/2000 | Duan et al. | |
| 6,319,187 B1 | 11/2001 | Scott | |
| 6,858,626 B2 | 2/2005 | Xue et al. | |
| 6,867,300 B2 | 3/2005 | Godfrey, Jr. et al. | |
| 6,949,579 B2 | 9/2005 | Dutruc-Rosset et al. | |
| 7,132,546 B2 | 11/2006 | Kato et al. | |
| 7,160,833 B2 | 1/2007 | Wagner et al. | |
| 7,173,031 B2 | 2/2007 | Borzilleri et al. | |

(Continued)

FOREIGN PATENT DOCUMENTS

| | | |
|---|---|---|
| WO | WO 2005/117867 | 12/2005 |
| WO | WO 2006/128129 | 11/2006 |

OTHER PUBLICATIONS

Han, S.-Y, et al., "Recent development of peptide coupling reagents in organic synthesis," Tetrahedron 60 (2004) pp. 2447-2467.

Cai, Zhen-Wei, et al., "Discovery of orally active pyrrolopyridine- and aminopyridine-based Met kinase inhibitors," Bioorganic and Medicinal Chemistry Letters 18 (2008) pp. 3224-3229.

Williams, David K, et al., "Design, synthesis and structure-activity relationships of novel biarylamine-based Met kinase inhibitors," Bioorganic and Medicinal Chemistry Letters, 20 (2010) pp. 2998-3002.

Schroeder, Gretchen M. et al., J. Medicinal Chemistry, 52 (2009) pp. 1251-1254.

(Continued)

*Primary Examiner* — Heidi Reese
(74) *Attorney, Agent, or Firm* — Gary D. Greenblatt

(57) ABSTRACT

Disclosed herein is a process for preparing a compound of Formula (I), comprising the steps of: (a) reacting an aniline compound of Formula (II) and an carboxylic acid compound of Formula (III) or an activated carboxylic acid compound thereof, to provide a compound of Formula (IV); and (b) converting said protected amine group attached to said compound of Formula (IV) to an amine group to provide said compound of Formula (I); wherein PAm is a protected amine group. Processes to prepare the compounds of Formulae (II), (III), and (IV) are also disclosed.

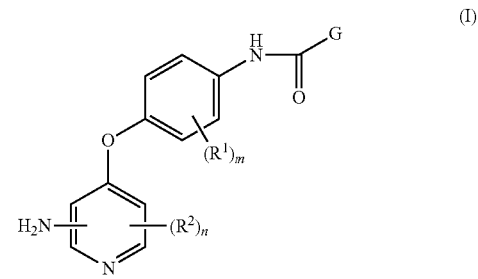

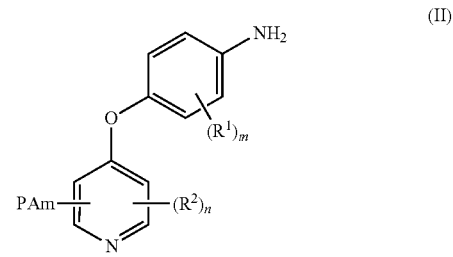

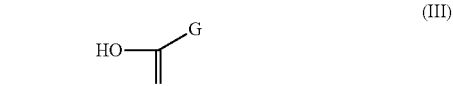

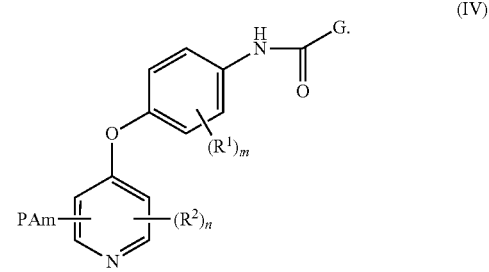

9 Claims, No Drawings

(56) References Cited

U.S. PATENT DOCUMENTS

| | | | |
|---|---|---|---|
| 7,211,666 | B2 | 5/2007 | Godfrey, Jr. et al. |
| 7,223,786 | B2 | 5/2007 | Meng et al. |
| 7,253,286 | B2 | 8/2007 | Funahashi et al. |
| 7,300,931 | B2 | 11/2007 | Hangauer, Jr. |
| 7,348,325 | B2 | 3/2008 | Cai et al. |
| 7,432,373 | B2 | 10/2008 | Crispino et al. |
| 7,439,246 | B2 | 10/2008 | Borzilleri et al. |
| 7,449,586 | B2 | 11/2008 | Chaturvedula et al. |
| 7,459,562 | B2 | 12/2008 | Borzilleri et al. |
| 7,470,693 | B2 | 12/2008 | Borzilleri et al. |
| 7,547,782 | B2 | 6/2009 | Borzilleri et al. |
| 7,566,784 | B2 | 7/2009 | Borzilleri et al. |
| 7,579,473 | B2 | 8/2009 | Bannen et al. |
| 7,691,870 | B2 | 4/2010 | Buchstaller et al. |
| 7,732,613 | B2 | 6/2010 | Kim |
| 2005/0038035 | A1 | 2/2005 | Takasugi et al. |
| 2006/0009453 | A1 | 1/2006 | Geuns-Meyer et al. |
| 2007/0117802 | A1 | 5/2007 | Borzilleri et al. |
| 2007/0197537 | A1 | 8/2007 | Blake et al. |
| 2007/0238726 | A1 | 10/2007 | Blake et al. |
| 2008/0004273 | A1 | 1/2008 | Raeppel et al. |
| 2008/0064718 | A1 | 3/2008 | Saavedera et al. |
| 2008/0064729 | A1 | 3/2008 | Gould et al. |
| 2008/0114033 | A1 | 5/2008 | Borzilleri et al. |
| 2008/0249105 | A1 | 10/2008 | Bennabi et al. |
| 2008/0255208 | A1 | 10/2008 | Luemmen et al. |
| 2008/0312232 | A1 | 12/2008 | Kim et al. |
| 2008/0319188 | A1 | 12/2008 | Matsushima et al. |
| 2009/0247526 | A1 | 10/2009 | Aicher et al. |

OTHER PUBLICATIONS

Kim, Kyoung Soon, et al., "Discovery of Pyrrolopyridine-Pyridone Based Inhibitors of Met Kinase: Synthesis, X-ray Crystallographic Analysis, and Biological Activities," J. Medicinal Chemistry ,51 (2008) pp. 5330-5341.

PCT Search Reports, Jul. 2010.

4-PYRIDINONE COMPOUNDS AND THEIR USE FOR CANCER

The present invention generally relates to processes for preparing pyridinone compounds.

Met, also referred to as hepatocyte growth factor receptor (HGFR), is expressed predominantly in epithelial cells but has also been identified in endothelial cells, myoblasts, hematopoietic cells, and motor neurons. Overexpression of hepatocyte growth factor and activation of Met has been associated with the onset and progression in a number of different tumor types as well as in the promotion of metastatic disease.

U.S. Patent Application Publication 2008/0114033 A1 discloses a pyridinone compound useful for treating Met-related cancers. The disclosed pyridinone compound, which comprises an amide linkage and an amine substituted pyridyl group, has the structure of Formula (Ia):

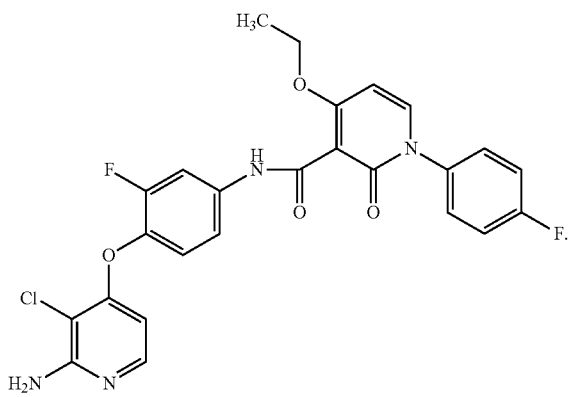

(Ia)

The reference also discloses a multistep synthesis process for preparing the pyridinone compound. This process includes the reaction between an aniline compound and a carboxylic acid compound to form the amide linkage in the compound of Formula (Ia). The disclosed process also includes a Hofmann Rearrangement reaction to convert an amide substituent to an amine group, to provide the amine substituted pyridyl group in the structure of Formula (Ia).

There are difficulties associated with the adaptation of the multistep synthesis disclosed in U.S. Patent Application Publication 2008/0114033 A1 to a larger scale synthesis, such as production in a pilot plant or on a manufacturing scale. One difficulty is that the Hofmann Rearrangement step was not readily adaptable to commercial scale synthesis. Further, there is a continuing need to find a process that provides higher yields in order to improve manufacturing economics and/or reduce waste. Preferably, a new process will employ less expensive starting materials.

Desired is a process that is suitable for preparing larger quantities of the pyridinone compound of Formula (I) than is typically prepared by laboratory scale processes. Also desired is a process that provides higher yields of the pyridinone compound of Formula (I) than the previously disclosed processes.

The present invention is directed to one or both of these, as well as other important aspects.

SUMMARY OF THE INVENTION

Described herein is a process for preparing a compound of Formula (I):

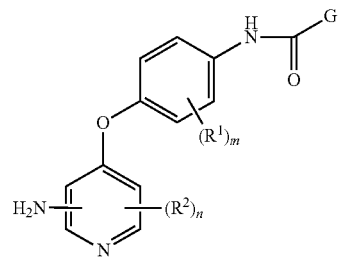

(I)

comprising the steps of:
(a) reacting a carboxylic acid compound of Formula (III):

(III)

or an activated carboxylic acid compound thereof, and an aniline compound of Formula (II):

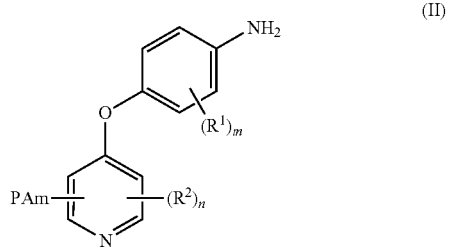

(II)

wherein PAm is a protected amine group, to provide a compound of Formula (IV):

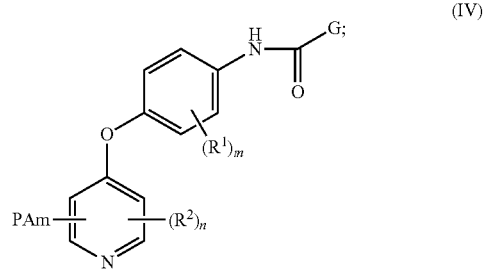

(IV)

and
(b) converting said protected amine group attached to said compound of Formula (IV) to an amine group to provide said compound of Formula (I);
wherein: G is

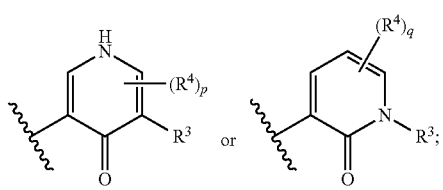

each $R^1$ is independently alkyl, haloalkyl, halogen, or CN;
each $R^2$ is independently alkyl, haloalkyl, halogen, or CN;

$R^3$ is phenyl substituted with alkyl, haloalkyl, halogen, or CN;
each $R^4$ is independently alkyl, haloalkyl, alkoxy, halogen, or CN;
m is zero, 1, 2, 3, or 4;
n is zero, 1, 2, or 3;
p is zero, 1 or 2; and
q is zero, 1, 2, or 3.

Also disclosed are compounds useful in the hereinabove process and processes to prepare these compounds.

DETAILED DESCRIPTION

Listed below are definitions of various terms used to describe the present invention. These definitions apply to the terms as they are used throughout the specification (unless they are otherwise limited in specific instances) either individually or as part of a larger group.

The term "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl, ethyl, propyl, isopropyl, n-butyl, t-butyl, pentyl, hexyl, isohexyl, heptyl, octyl, nonyl, decyl, and dodecyl.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "$C_0$-$C_4$alkyl" includes a bond and an alkyl group containing 1 to 4 carbon atoms, and the term "$C_1$-$C_4$alkyl" refers to alkyl groups containing 1 to 4 carbon atoms. Exemplary lower alkyl groups include, but are not limited to, for example, methyl, ethyl, propyl, isopropyl, n-butyl, t-butyl, and isobutyl.

The term "halogen" and "halo" refer to fluorine, chlorine, bromine, and iodine.

The term "haloalkyl" refers to an alkyl group substituted at one or more positions with halo substituents. Exemplary haloalkyl groups include, but are not limited to, haloalkyls having a single halo substituent such as —$CH_2F$, —$CH_2Cl$, and —$CH_2Br$, and haloalkyls having multiple halo substituents such as —$CHF_2$, —$CF_3$, —$CHCl_2$, and —$CCl_3$.

The term "cyano" refers to —CN.
The term "amine" refers to —$NH_2$.
The term "carboxylic acid" refers to —C(O)OH, which may be depicted as:

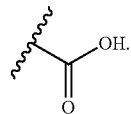 [SMILES: *C(=O)O]

The term "alkoxy" refers to —O-alkyl. Examples of alkoxy groups include, but are not limited to, methoxy, ethoxy, n-propoxy, n-butoxy, and t-butoxy.

The term "amide linkage" refers to —NHC(O)—, which may be depicted as:

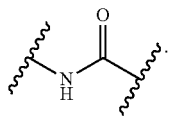 [SMILES: *NC(*)=O]

The pyridinone compound of Formula (V) may exist in the enol form represented by the formula below:

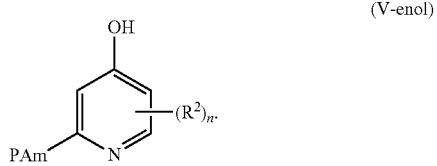

(V-enol)

As used herein, the terms "compound of Formula (V)" and "compound of Formula (V-enol)" refer to the compound of Formula (V) in the keto form, the enol form, or any mixture comprising the keto and enol forms.

One aspect of the present invention relates to a process for preparing the compound of Formula (I) in which the compound of Formula (I) comprises an amide linkage and a pyridyl group substituted with an amine.

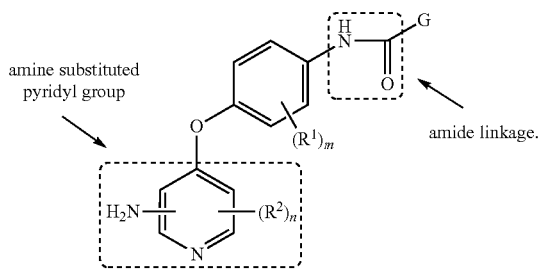

The amide linkage in the compound of Formula (I) can be prepared by reacting the carboxylic acid compound of Formula (III) or an activated carboxylic acid compound thereof, with the aniline compound of Formula (II), wherein the aniline compound of Formula (II) comprises a pyridyl group having a protected amine group (PAm). The amide linkage is formed by reaction of the amine group attached to the phenyl ring (the aniline group of the compound of Formula (II)) and the carboxylic acid group of the compound of Formula (III) or an activated carboxylic acid group thereof. The protected amine group minimizes and/or eliminates competing side reactions between the amine functionality attached to the pyridyl group of the compound of Formula (II) and the carboxylic acid compound of Formula (III) or an activated carboxylic acid compound thereof.

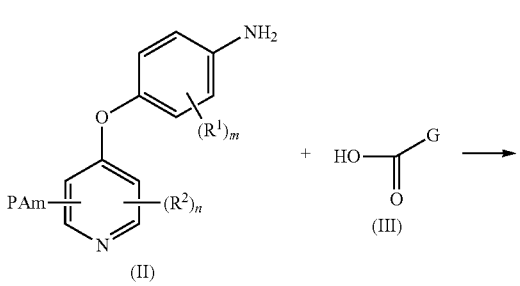

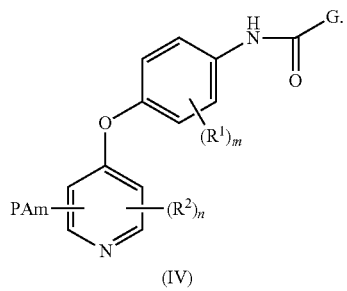

(IV)

After formation of the amide linkage, the protected amine group (PAm) attached to the compound of Formula (IV) is converted to an amine group to provide the compound of Formula (I):

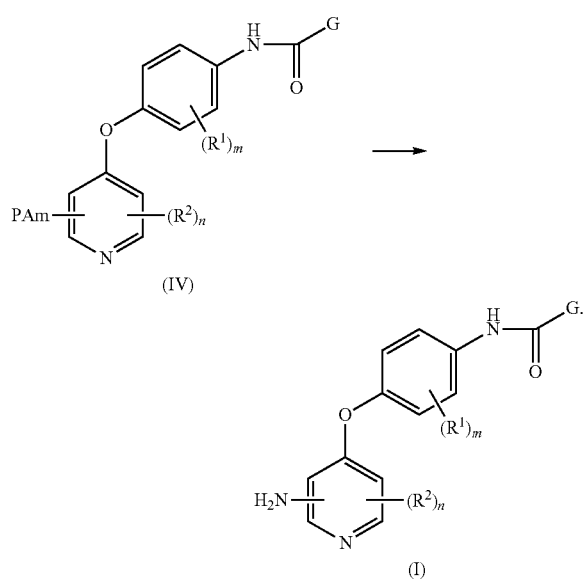

The protected amine group (PAm) comprises a nitrogen atom that is bonded directly to the pyridyl ring and further comprises one or two blocking groups attached to the nitrogen atom. The blocking groups minimize or eliminate reactions of the nitrogen atom bonded to the pyridyl ring during the formation of the amide linkage between the aniline compound and the carboxylic acid compound. The protected amine group is nonreactive or substantially nonreactive during the formation of the amide linkage. After the formation of the amide linkage, the blocking groups are removed to provide the amine substituted pyridyl group of the compound of Formula (I). The protected amine group expressly excludes groups in which the nitrogen atom is not directly attached to the pyridal ring, such as —C(O)NH$_2$.

Various protected amine groups may be employed in the process of the present invention. Examples of suitable protected amine groups include, but are not limited to, imines, alkylamines, arylamines, carbamates, amides, imides, benzylamines, allylamines, silylamines, phosphonamides, sulfonamides, and triazinanones.

TABLE 1

Protected Amine Groups

| Protected as | General formula | Examples |
|---|---|---|
| Imine | —N=C(R)$_2$ | R = H, alkyl, aryl |
| | | Benzophenone imine (R = Ph) |
| Alkylamine arylamine | —NH—R or N(R)$_2$ | R = alkyl, aryl |
| | | t-Butylamine (R = t-butyl) |
| | | Benzyl (R = CH$_2$Ph) |
| | | p-Methoxybenzyl (R = CH$_2$-anisole) |
| Carbamate | —NHCOOR or —N(COOR)$_2$ | R = H, alkyl, aryl |
| | | BOC (R = t-butyl) |
| | | Ethylcarbamate (R = Et) |
| Amide | —NHCOR | R = H, alkyl, aryl |
| | | Pivolate (R = t-butyl) |
| | | Triflate (R = COCF$_3$) |
| | | Formamide (R = H) |
| Imide | —N(COR)$_2$ | R = H, alkyl, aryl |
| | | Phthalimide |
| Benzylamine or Allylamine | —NH—CH$_2$R or —N(CH$_2$R)$_2$ | R = vinyl, aryl |
| | | Benzhydryl (R = Ph) |
| | | Allyl and diallyl (R = CH=CH$_2$) |
| Silylamine | —NHSiR$_3$ or —N(SiR$_3$)$_2$ | R = alkyl |
| | | HMDS (R = Me) |
| Phosphonamide | —NHPO(R)$_2$ | R = alkoxy |
| | | (R = OEt) |
| Sulfonamide | —NHSO$_2$R | (R = CH$_2$CH$_2$SiMe$_3$) |
| | | Nosyl (R = p-nitrophenyl) |
| Triazinanones | (structure) | R = Benzyl, alkyl |

Preferred protected amine groups include imines, amides, carbamates, imides, sulfonamides, silylamines, benzylamines, allylamines, phosphonamides, and triazinanones. More preferred protected amine groups include imines, amides, carbamates, imides, and sulfonamides.

Step I: Formation of Amide Linkage

Various synthetic routes can be employed to form the amide linkage by the reaction of the carboxylic acid compound of Formula (III) and the aniline compound of Formula (II). One route is the reaction of the carboxylic acid compound of Formula (III) and the aniline compound of Formula (II), optionally in the presence of a suitable catalyst, such as an acid or a base catalyst. Another route is the reaction of an activated carboxylic acid compound of Formula (III) and the aniline compound of Formula (II). The activated carboxylic acid compound of Formula (III) can be prepared by contacting the carboxylic acid compound of Formula (III) with an activating agent to provide the activated carboxylic acid compound of Formula (III), prior to reaction with the aniline compound of Formula (II). As used herein, the step of reacting a carboxylic acid compound of Formula (III) and an aniline compound of Formula (II) includes both the reaction between the carboxylic acid compound of Formula (III) and/or the activated carboxylic acid compound thereof, and the aniline compound of Formula (II).

In one embodiment, the process of the present invention comprises preparing the compound of Formula (I) by a) reacting an activated carboxylic acid compound of Formula (III) and an aniline compound of Formula (II) to provide a compound of Formula (IV); and b) converting the protected amine group attached to said compound of Formula (IV) to an amine group to provide said compound of Formula (I). For example, an activated carboxylic acid compound of Formula (IIIc), such as an acid halide compound of Formula (IIIc), can be reacted with the aniline compound of Formula (II) to provide the compound of Formula (IV).

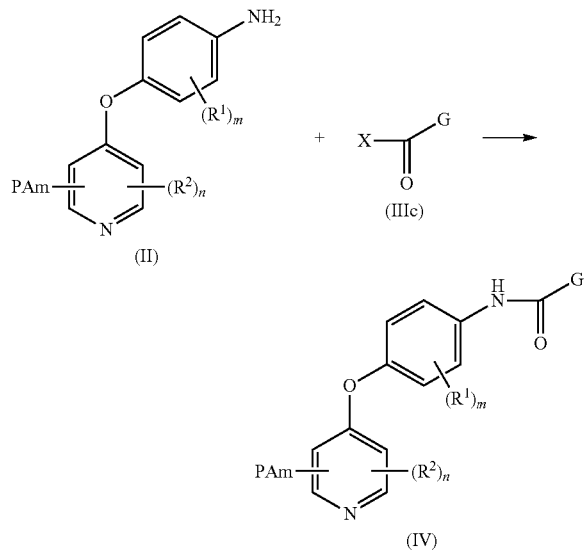

wherein X is an activating group such as, for example, chlorine.

Methods for activating carboxylic acid groups to prepare amide linkages, including activating agents, solvents, and reaction conditions, are described in Han, S.-Y. et al., *Tetrahedron* 60 (2004) 2447-2467.

The activated carboxylic acid compounds of Formula (IIIc) can be prepared by contacting the carboxylic acid compound of Formula (III) with various adjuvants including, but not limited to, acid halides including acid chlorides such as oxalyl chloride (COCl)$_2$, sulfonylchloride (SO$_2$Cl), Vilsmeier reagent (N-chloromethylene-N,N-dimethyl ammonium chloride), phosphorylchloride (POCl$_3$), PO(OEt)$_2$Cl, and pivaloylchloride (t-BuCOCl); uronium salts such as O-benzotriazol-1-yl-1,1,3,3-tetramethyluronium tetrafluoroborate (TBTU) and O-(7-azabenzotriazol-1-yl)-1,1,3,3-tetramethyluronium hexafluorophosphate (HATU); dicarbodiimides such as dicyclohexylcarbodiimide and N-(3-dimethylaminopropyl)-N'-ethyldicarbodiimide, with or without 1-hydroxybenzotriazole (HOBt) or 1-hydroxy-7-azabenzotriazole (HOAt); 2-hydroxypyridine-1-oxide; 4-(4,6-dimethoxy[1,3,5]triazin-2-yl)-4-methylmorpholinium chloride (DMTMM); chloroformates (general formula ROCOCl) such as tert-butylchloroformate, iso-butylchloroformate, and isopropylchloroformate; propylphosphonic anhydride; diethyl chlorophosphate; Mitsunobu reagents including diethylazodicarboxylate and triphenylphosphine; and trimethylsilyl-isothiocyanate (TMS-ITC). Preferred reagents include dicyclohexylcarbodiimide, N-(3-dimethylaminopropyl)-N'-ethyldicarbodiimide, Vilsmeier reagent, oxalyl chloride, thionyl chloride, propylphosphonic anhydride, diethyl chlorophosphate, pivaloyl chloride, chloroformates including tert-butyl chloroformate, iso-butylchloroformate, isopropylchloroformate, trimethylsilyl-isothiocyanate, and Mitsunobu reagents (diethylazodicarboxylate and triphenylphosphine). More preferred reagents include Vilsmeier reagents, oxalyl chloride, and thionyl chloride.

The reaction of the carboxylic acid compound of Formula (III) or the activated carboxylic acid compound of Formula (IIIc) with the aniline compound of Formula (II) can be conducted in the presence of various synthesis adjuvants, including, for example, organic bases such as triethyl amine, potassium tert-butoxide, sodium 2-ethylhexanoate, and N,N-diisopropylethylamine (DIPEA); and inorganic bases such as sodium carbonate and cesium carbonate. Other suitable adjuvants include acylation catalysts such as 4-dimethylaminopyridine (DMAP), 1hydroxybenzotriazole, 2-pyridone, 1,4-diazabicyclo[2.2.2]octane (DABCO), 1,8-diazabicylco [5.4.0]undec-7-ene (DBU), and 2,6-lutidine. Preferred synthesis adjuvants include organic bases such as triethyl amine, potassium tert-butoxide, and sodium 2-ethylhexanoate; and acylation catalysts such as 2-pyridone, 4-dimethylaminopyridine, 1-hydroxybenzotriazole, 1,4-diazabicyclo[2.2.2]octane, 1,8-diazabicylco [5.4.0]undec-7-ene, and 2,6-lutidine. Most preferred synthesis adjuvants include sodium 2-ethylhexanoate.

The reaction between a carboxylic acid compound of Formula (III) or an activated carboxylic acid compound Formula (IIIc), and the aniline compound of Formula (II) can be conducted in various solvents or mixtures thereof. Examples of suitable solvents include, but are not limited to, polar aprotic solvents such as dimethyl formamide, dimethyl sulfoxide, and N-methylpyrrolidinone; etheral solvents such tetrahydrofuran, 2-methyl tetrahydrofuran, methyl t-butyl ether, and diethoxymethane; hydrocarbons such as benzene, toluene, hexanes, and heptane; halogenated solvents such as dichloromethane and 1,2-dichloroethane; acetates such as ethyl acetate, isopropyl acetate, and butyl acetate, and other solvents such as acetonitrile, methyl vinyl ketone, N,N-dimethylacetamide; and mixtures thereof. Preferred solvents include etheral solvents such tetrahydrofuran, 2-methyl tetrahydrofuran, and diethoxymethane; hydrocarbons such as toluene and heptane; and halogenated solvents such as dichloromethane and 1,2-dichloroethane. More preferred solvents include halogenated solvents such as dichloromethane and 1,2-dichloroethane.

Suitable reaction temperatures for the reaction between the carboxylic acid compound of Formula (III) or the activated carboxylic acid compound thereof, and the aniline compound of Formula (II) include temperatures in the range of from about −50° C. to about 150° C., preferably in the range of from −25° C. to about 100° C., and more preferably in the range of from 0° C. to 50° C.

In one embodiment, the activated carboxylic acid compound of Formula (IIIa) is prepared by reacting the carboxylic acid compound of Formula (III) and oxalyl chloride in a halogenated solvent, such as dichloromethane, and/or dimethyl formamide at a temperature in the range of from −20° C. to −40° C.

Step II: Removal of Protecting Group to Generate Amine

After formation of the compound of Formula (IV), the protected amine group attached to the pyridyl group of said compound is converted to an amine group to provide the compound of Formula (I). Various methods may be employed to convert the protected amine group to the amine group without affecting the amide linkage. Examples of suitable methods include:

a) Treatment with organic, inorganic, or Lewis acids in the presence of water. Suitable acids include, for example, formic acid, acetic acid, methanesulfonic acid, trifluoroacetic acid, citric acid, hydrochloric acid, sulfuric acid phosphoric acid, magnesium triflate, and lithium bromide.

b) Treatment with organic, inorganic, or Lewis acids without the addition of water. Suitable acids include, for example, formic acid, acetic acid, magnesium triflate, and lithium bromide.

c) Treatment with organic or inorganic bases, including, for example, carbonates ($M_mCO_3)_n$) such as $K_2CO_3$, $Na_2CO_3$, and $Cs_2CO_3$; hydroxides ($M_m(OH)_n$) such as KOH, NaOH, and LiOH; alcoholates ($M_m(OR)_n$) such as $NaOCH_3$, KO(t-butyl), and Na(O-ethyl); phosphates ($M_m(PO_4)_n$) such as $K_2HPO_4$ and $K_3PO_4$; and amines such as triethylamine, N,N-diisopropylethylamine, N-methyl morpholine, 1,4-diazabicyclo [2.2.2]octane (DABCO), and 1,8-diazabicylco[5.4.0]undec-7-ene.
d) Treatment by heating in the presence of water.
e) Treatment with fluoride.
f) Treatment with oxidants such as ceric ammonium nitrate (CAN) and 2,3-dichloro-5,6-dicyano-p-benzoquinone (DDQ).

Suitable solvents for conversion of the protected amine group include, for example, polar aprotic solvents such as dimethylformamide, dimethyl sulfoxide, and N-methylpyrrolidinone; etheral solvents such as tetrahydrofuran, 2-methyl tetrahydrofuran, methyl t-butyl ether, and diethoxymethane; hydrocarbons such as toluene, heptane, benzene, and hexanes; halogenated solvents such as dichloromethane and 1,2-dichloroethane; acetates such as ethyl acetate, isopropyl acetate, and butyl acetate; alcohols such as methanol, ethanol, and isopropanol; and other solvents such as acetonitrile, methyl vinyl ketone, and N,N-dimethylacetamide; and mixtures thereof. Preferred solvents include tetrahydrofuran, 2-methyl tetrahydrofuran, methyl t-butyl ether, toluene, N-methylpyrrolidinone, dimethylformamide, N,N-dimethylacetamide, and ethanol.

Suitable reaction temperatures for converting a protected amine group to an amine group include temperatures in the range of from about −78° C. to about 200° C., preferably in the range of from −25° C. to about 150° C., and more preferably in the range of from 0° C. to 100° C.

The compound of Formula (I) and the compound of Formula (IV) can be isolated and/or purified by various methods known in the art. Suitable methods include chromatography, crystallization, filtration, and distillation.

In one embodiment, the process for preparing a compound of Formula (I) employs the aniline compound of Formula (II) and/or the compound of Formula (IV) wherein the protected amine group, PAm, is —NH—$R^b$, —NHC(O)$OR^a$, —NHC(=O)$R^a$, —NH($CH_2R^c$), —NHSi($R^d)_3$, —NH(PO($OR^a)_2$), —$NHSO_2R^e$, —N($R^b)_2$, —N(C(O)$OR^a)_2$, —N(C(O)$R^a)_2$, —N($CH_2R^c)_2$, —N(Si($R^d)_3)_2$, —N=C($R^a)_2$, or

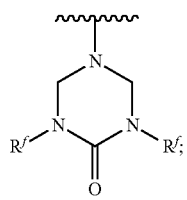

wherein: each $R^a$ is independently H, alkyl, haloalkyl, benzyl, and/or aryl; each $R^b$ is independently alkyl, haloalkyl, benzyl, methoxybenzyl, and/or aryl; each $R^c$ is independently allyl or alkoxy; each $R^d$ is independently alkyl; $R^e$ is alkyl, alkyl substituted with —Si(alkyl)$_3$, phenyl, or nitrophenyl; and each $R^f$ is independently alkyl or benzyl. Preferably, PAm is an imine, imide, carbamate, amide, or sulfonamide. More preferably, PAm is an imine or imide.

In one embodiment, the process for preparing a compound of Formula (I) is employed to prepare compounds of Formula (I) in which $R^1$ is halogen and m is zero, 1, or 2. Preferably, m is 1. Preferably, $R^1$ is F or Cl, and more preferably F. More preferably, $R^1$ is F and m is 1.

In one embodiment, the process for preparing a compound of Formula (I) is employed to prepare compounds of Formula (I) in which $R^2$ is halogen and n is zero, 1, or 2. Preferably, n is 1. Preferably, $R^2$ is F or Cl, and more preferably F. More preferably, $R^2$ is F and n is 1.

In one embodiment, the process for preparing a compound of Formula (I) is employed to prepare compounds of Formula (I) in which $R^3$ is phenyl substituted with $C_1$-$C_4$ alkyl, $C_1$-$C_3$ halo alkyl, halogen, or CN; preferably, $R^3$ is methyl, ethyl, trifluoromethyl, pentafluoroethyl, halogen, or CN; and more preferably, $R^3$ is methyl, trifluoromethyl, F, Cl, or CN.

In one embodiment, the process for preparing a compound of Formula (I) is employed to prepare compounds of Formula (I) in which $R^3$ is phenyl substituted with halogen; more preferably, $R^3$ is phenyl substituted with F or Cl; and still more preferably, $R^3$ is a fluorophenyl, including, for example, 4-fluorophenyl.

In one embodiment, the process for preparing a compound of Formula (I) is employed to prepare the pyridinone compound N-(4-(2-amino-3-chloropyridin-4-yloxy )-3-fluorophenyl)-4-ethoxy-1-(4-fluorophenyl)-2-oxo-1,2-dihydropyridine-3-carboxamide, which has the structure represented by Formula (Ia)

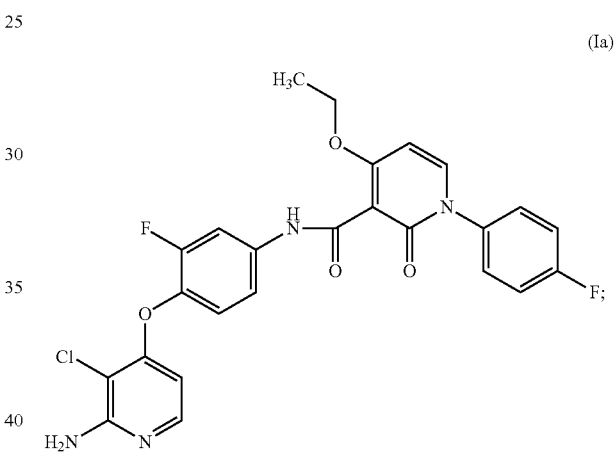

or the pyridinone compound N-(4-(2-Amino-3-chloropyridin-4-yloxy)-3-fluorophenyl )-5-(4-fluorophenyl)-4-oxo-1,4-dihydropyridine-3-carboxamide, which has the structure represented by Formula (Ib)

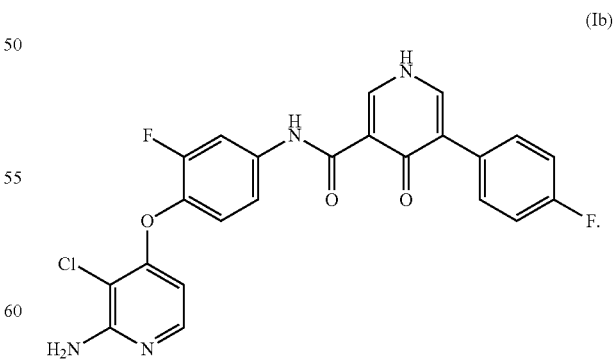

U.S. Patent Application Publication 2008/0114033 A1 discloses the Compound of Formula (Ia) and is incorporated herein in its entirety. U.S. Provisional Patent Application 61/022,848 discloses the Compound of Formula (Ib) and prodrugs thereof, and is incorporated herein in its entirety. The present application claims priority to U.S. Provisional Patent application 61/022,848. These compounds are Met kinases inhibitors and are useful in the treatment of cancers, such as, for example, bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, malignant fibrous histiocytoma (MFH), fibrosarcoma, glioblastomas/astrocytomas, melanoma, and mesothelioma.

In one embodiment, a process is provided for preparing N-(4-(2-amino-3-chloropyridin-4-yloxy)-3-fluorophenyl)-4-ethoxy-1-(4-fluorophenyl)-2-oxo-1,2-dihydropyridine-3-carboxamide, the compound of Formula (Ia)

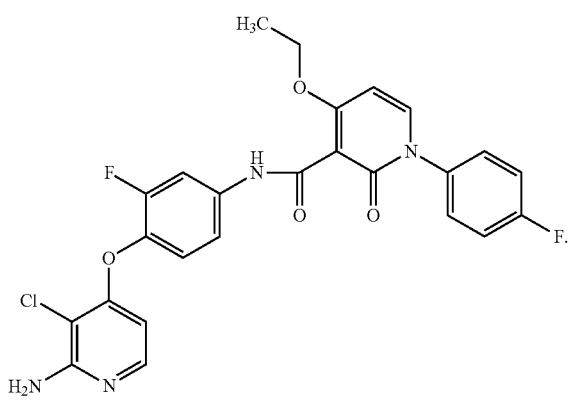

(Ia)

In this embodiment, the process comprises the steps of: (a) reacting an aniline compound of Formula (IIb):

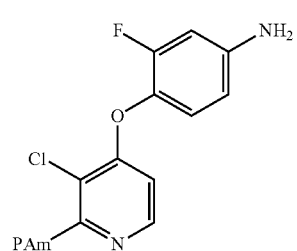

(IIb)

and an carboxylic acid compound of Formula (IIIa):

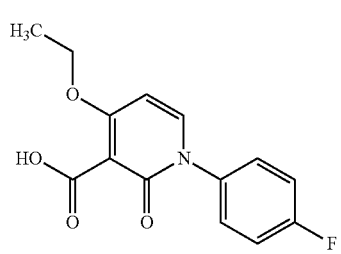

(IIIa)

or an activated carboxylic acid compound thereof, to provide a compound of Formula (IVa):

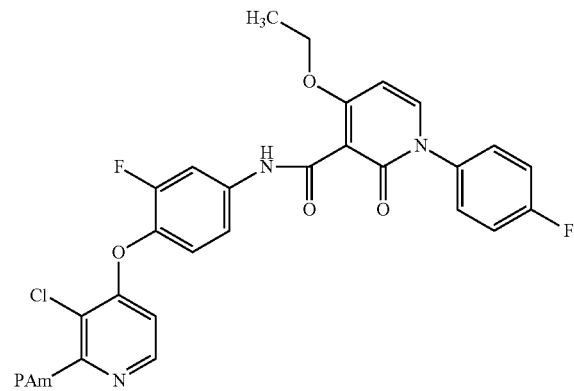

(IVa)

wherein PAm is a protected amine group; and (b) converting said protected amine group attached to said compound of Formula (IVa) to an amine group to provide said compound of Formula (Ia).

In one embodiment, a process is provided for preparing a compound of Formula (Ib):

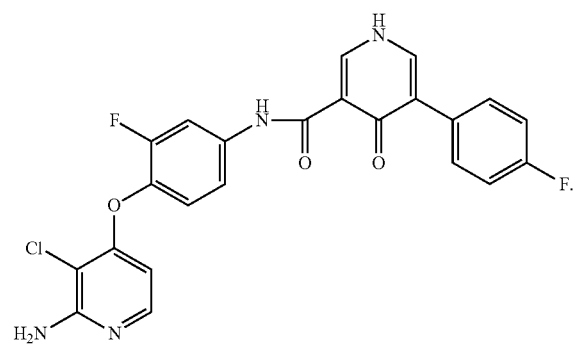

(Ib)

In this embodiment, the process comprising the steps of: a) reacting an aniline compound of Formula (IIb):

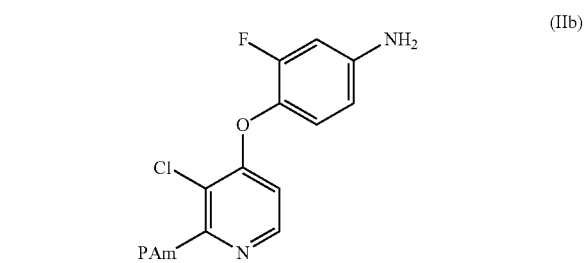

(IIb)

with an carboxylic acid compound of Formula (IIIb):

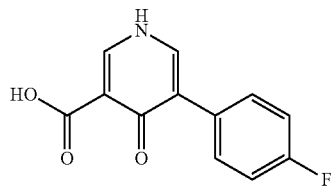

(IIIb)

or an activated carboxylic acid compound thereof, to provide a compound of Formula (IVb):

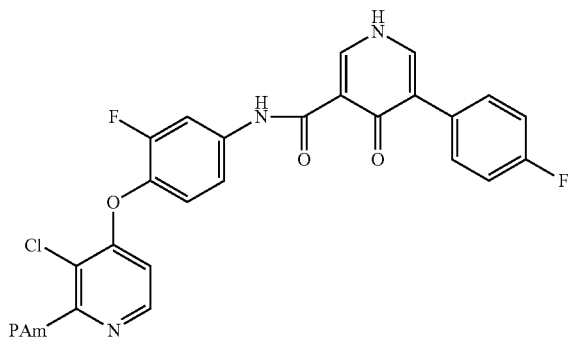

wherein PAm is a protected amine group; and
b) converting said protected amine group attached to said compound of Formula (IVb) to an amine group to provide said compound of Formula (Ib).

The compound of Formula (Ib) may be provided as a prodrug, as disclosed in U.S. Provisional Application 61/022,848.

One embodiment provides a compound of Formula (VIIIa) having the structure:

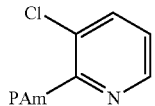

wherein PAm is defined hereinabove. One example of a compound of this embodiment is 3-chloro-2-(diphenylmethyleneamino) pyridin-4(1H)-one, which has the structure of Formula (3A):

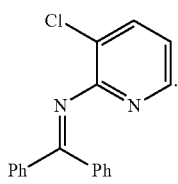

In another embodiment, a process is provided comprising the step of reacting 2,3-dichloropyridine and benzophenone imine to provide 3-chloro-2-(diphenylmethyleneamino) pyridin-4(1H)-one.

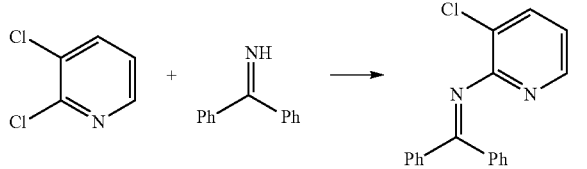 [SMILES: Clc1cccnc1Cl ; N=C(c1ccccc1)c1ccccc1 ; Clc1cccnc1N=C(c1ccccc1)c1ccccc1]

In the process of this embodiment, various solvents, synthesis adjuvants, and reaction conditions can be employed.

Examples of suitable solvents include, but are not limited to, polar aprotic solvents such as dimethylformamide, dimethyl sulfoxide, and N-methylpyrrolidinone; etheral solvents such as tetrahydrofuran, 2-methyl tetrahydrofuran, and diethoxymethane; hydrocarbons such as toluene, heptane, benzene, and hexanes; halogenated solvents such dichloromethane and 1,2-dichloroethane; acetates such as ethyl acetate, isopropyl acetate, and butyl acetate; other solvents such as acetonitrile and methyl vinyl ketone; or mixtures thereof. The reaction can be conducted in the presence of various synthesis adjuvants such as catalysts, bases, and/or ligands. Examples of suitable catalysts include, but are not limited to, palladium catalysts such as palladium acetate and tetrakis(triphenylphosphine)palladium; copper catalysts such as copper (I) halides and copper (II) trifluoromethanesulfonate; and nickel catalysts such as Bis(1,5-cyclooctadiene) nickel (0); which can be present in range of from 0.0001 to 1.5 equivalents. Examples of suitable ligands include, but are not limited to, phosphine ligands such as 2,2'-bis(diphenylphosphino)-1,1'-binaphthylene, $P(alkyl)_2(phenyl)$, $P(alkyl)(phenyl)_2$, and $P(phenyl)_3$; and nitrogen heterocycles such as imidazole and hydroxy pyridine, which can be present in the range of from 0.0001 to 1.5 equivalents. Examples of suitable bases include, but are not limited, inorganic bases such as sodium carbonate, and cesium carbonate; and organic bases such as triethylamine and potassium butoxide; which can be present in the range of from 1 to 10 equivalents. Preferably, the reaction of this embodiment is conducted in at least one solvent selected from tetrahydrofuran, 2-methyl tetrahydrofuran, diethoxymethane, toluene, and/or heptane; and more preferably, tetrahydrofuran, 2-methyl tetrahydrofuran, and/or diethoxymethane. Preferably, the reaction of this embodiment is conducted in the presence of at least base selected from sodium carbonate and/or cesium carbonate. Preferably, the reaction of this embodiment is conducted in the presence of at least one palladium catalyst, for example, palladium acetate and/or tetrakis(triphenylphosphine)palladium. Preferably, the reaction of this embodiment is conducted in the presence of at least one phosphine ligand selected from 2,2'-bis(diphenylphosphino)-1,1'-binaphthylene, $P(alkyl)_2(phenyl)$, $P(alkyl)(phenyl)_2$, and $P(phenyl)_3$. For example, the reaction of this embodiment can be conducted in the presence of cesium carbonate, palladium acetate, and 2,2'-bis (diphenylphosphino)-1,1'-binaphthylene in at least one solvent selected from tetrahydrofuran, 2-methyl tetrahydrofuran, and/or diethoxymethane. In the present embodiment, the reaction to prepare 3-chloro-2-(diphenylmethyleneamino) pyridin-4(1H)-one can be conducted at temperatures in the range of from about −78° C. to about 200° C., preferably in the range of from −25° C. to about 150° C., and more preferably in the range of from 0° C. to 100° C. The reaction product can be separated and purified by methods known in the art.

One embodiment provides a compound of Formula (Vb) having the structure:

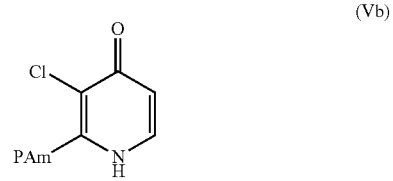

wherein PAm is defined hereinabove. One example of a compound of this embodiment is 3-chloro-2-(diphenylmethyleneamino)pyridin-4(1H)-one, which has the structure of Formula (3B):

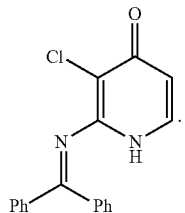

(3B)

One embodiment provides a compound of Formula (VIIa)

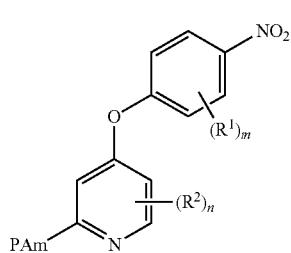

(VIIa)

wherein each $R^1$ is independently alkyl, haloalkyl, halogen, or CN; each $R^2$ is independently alkyl, haloalkyl, halogen, or CN; m is zero, 1, 2, 3, or 4; n is zero, 1, 2, or 3; and PAm is a protected amine group. Preferably, $R^1$ is halogen, m is 1, $R^2$ is halogen, and n is 1. Preferably, PAm is an imine, imide, carbamate, amide, or sulfonamide. More preferably, PAm is an imine or imide.

In one embodiment, provided is a compound of Formula (VIIb):

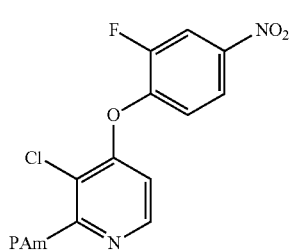

(VIIb)

wherein PAm is defined hereinabove. Preferably, PAm is an imine, imide, carbamate, amide, or sulfonamide. More preferably, PAm is an imine or imide.

One embodiment provides an aniline compound of Formula (II)

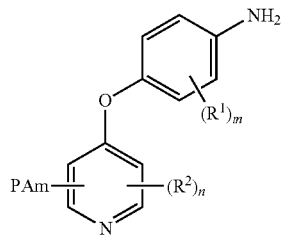

(II)

or a salt thereof; and/or an aniline compound of Formula (IIa)

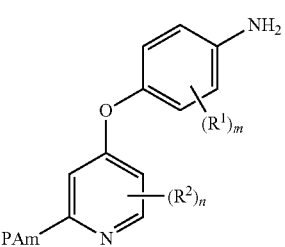

(IIa)

or a salt thereof, wherein each $R^1$ is independently alkyl, haloalkyl, halogen, or CN; each $R^2$ is independently alkyl, haloalkyl, halogen, or CN; m is zero, 1, 2, 3, or 4; n is zero, 1, 2, or 3; and PAm is a protected amine group. Preferably, $R^1$ is halogen, m is 1, $R^2$ is halogen, and n is 1. Preferably, PAm is an imine, imide, carbamate, amide, or sulfonamide. More preferably, PAm is an imine or imide.

In one embodiment, provided is the compound of Formula (IIc) or a salt thereof.

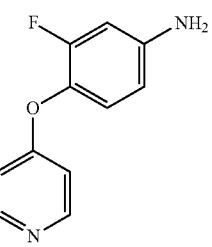

(IIc)

wherein PAm is defined hereinabove. Preferably, PAm is an imine, imide, carbamate, amide, or sulfonamide. More preferably, PAm is an imine or imide.

Preparation of Aniline Compounds of Formula (II)

The following reaction scheme shows various general synthetic routes for preparing the compound of Formula (VIIb), which is useful as a precursor to the compound of Formula (IIc).

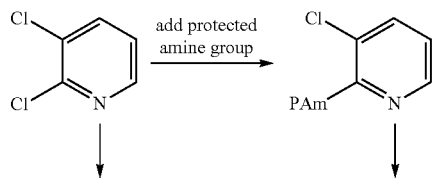

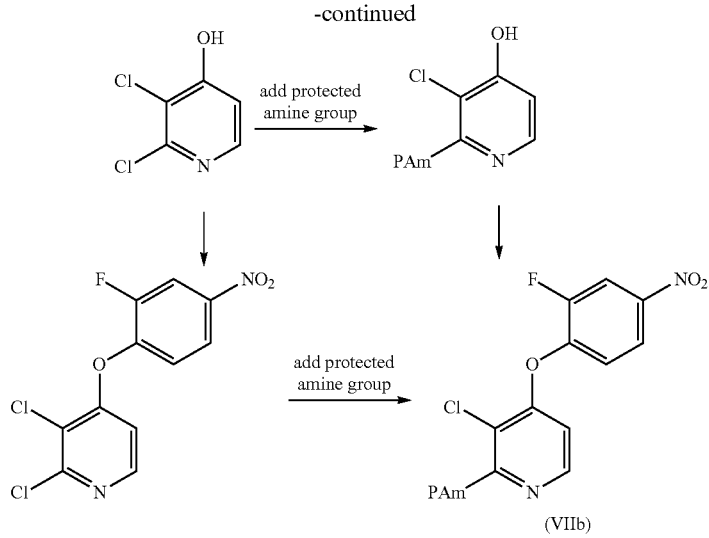

In one embodiment, a process is provided for preparing a compound of Formula (V), comprising the step of oxidizing a compound of Formula (VIII).

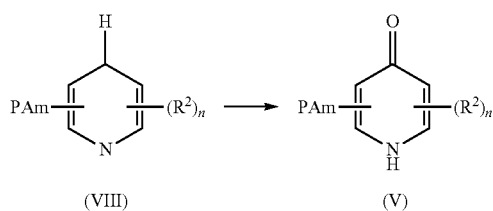

The compound of Formula (VII) converted to the compound of Formula (V) by deprotonation, followed by direct oxidation; or alternatively, by deprotonation, followed by boralation, and then oxidation. For example, the process of this embodiment can be employed to prepared 3-chloro-2-(diphenylmethyleneamino) pyridin-4(1H)-one by oxidizing 3-chloro-2-(diphenylmethyleneamino) pyridin-4(1H)-one.

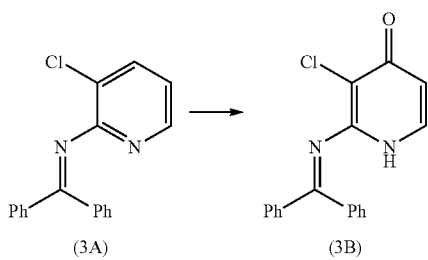 [SMILES: Clc1cccnc1N=C(c1ccccc1)c1ccccc1 ; O=c1cc[nH]c(N=C(c2ccccc2)c2ccccc2)c1Cl]

Various solvents, synthesis adjuvants, and reaction conditions can be employed in the process of this embodiment. Examples of suitable solvents include, but are not limited to, polar aprotic solvents such as dimethylformamide, dimethyl sulfoxide, and N-methylpyrrolidinone; etheral solvents such as tetrahydrofuran, 2-methyl tetrahydrofuran, and diethoxymethane; hydrocarbons such as toluene, heptane, benzene, and hexanes; and halogenated solvents such dichloromethane and 1,2-dichloroethane, or mixtures thereof. The reaction can be conducted in the presence of various synthesis adjuvants including oxidants such as hydrogen peroxide, sodium percarbonate, potassium peroxymonosulfate (Oxone™ compound), and sodium tetrafluoroborate; peroxides such as t-butyl hydrogen peroxide and m-chloroperoxybenzoic acid; trialkoxyborates; and/or lithium amides such as lithium diisopropylamide. Suitable amounts of peroxide, trialkoxyborates, and lithium amide include 1 to 4 equivalents each. Preferred solvents include tetrahydrofuran, 2-methyl tetrahydrofuran, diethoxymethane, toluene, and heptane, or a mixture thereof. Preferred oxidants include hydrogen peroxide, sodium percarbonate, and potassium peroxymonosulfate. For example, the process of this embodiment can be employed to prepare 3-chloro-2-(diphenylmethyleneamino) pyridin-4(1H)-one by reacting 3-chloro-2-(diphenylmethyleneamino) pyridin-4(1H)-one in the presence of 1-3 equivalents of lithium diisopropylamide, 1-4 equivalents of triisopropoxyborate, and an oxidizing agent selected from sodium percarbonate and/or potassium peroxymonosulfate in a solvent selected from tetrahydrofuran, 2-methyl tetrahydrofuran, diethoxymethane, toluene, and heptane, or a mixture thereof.

In another embodiment, a process is provided for preparing the compound of Formula (VIIb), comprising the step of reacting a compound of Formula (Vb) with 1,2-difluoro-4-nitrobenzene.

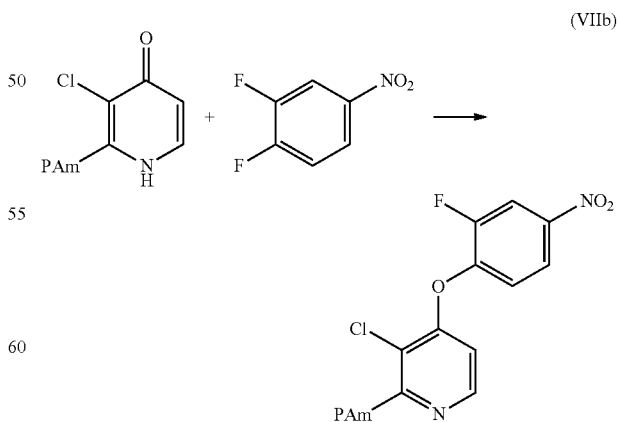

In the process of this embodiment, various solvents, synthesis adjuvants, and reaction conditions can be employed. Examples of suitable solvents include, but are not limited to, polar aprotic solvents such as dimethylformamide, dimethyl sulfoxide, and N-methylpyrrolidinone; etheral solvents such as tetrahydrofuran, 2-methyl tetrahydrofuran, and diethoxymethane; hydrocarbons such as toluene, heptane, benzene, and hexanes; halogenated solvents such dichloromethane and 1,2-dichloroethane; acetates such as ethyl acetate, isopropyl acetate, and butyl acetate; other solvents such as acetonitrile and methyl vinyl ketone; or mixtures thereof. The reaction can be conducted in the presence of various synthesis adjuvants including bases. Examples of suitable bases include, but are not limited, inorganic bases such as sodium carbonate, lithium carbonate, and cesium carbonate; and organic bases such as triethylamine and potassium butoxide. The process of the present embodiment can be conducted at temperatures in the range of from about −78° C. to about 200° C., preferably in the range of from −25° C. to about 150° C., and more preferably in the range of from 0° C. to 100° C. The reaction product can be separated and purified by methods known in the art. Preferably, the reaction of this embodiment is conducted in a solvent selected from dimethylformamide, dimethyl sulfoxide, and N-methylpyrrolidinone, or mixtures thereof. Preferably, the reaction of this embodiment is conducted in the presence of at least inorganic base, such as sodium carbonate, lithium carbonate, and/or cesium carbonate. For example, the process of the present embodiment can be conducted in the presence of lithium carbonate and/or cesium carbonate in a solvent selected from dimethyl formamide, N-methylpyrrolidinone, and mixtures thereof.

In another embodiment, a process is provided for preparing an aniline compound of Formula (II), comprising the step of converting a compound of Formula (VII) to a compound of Formula (II)

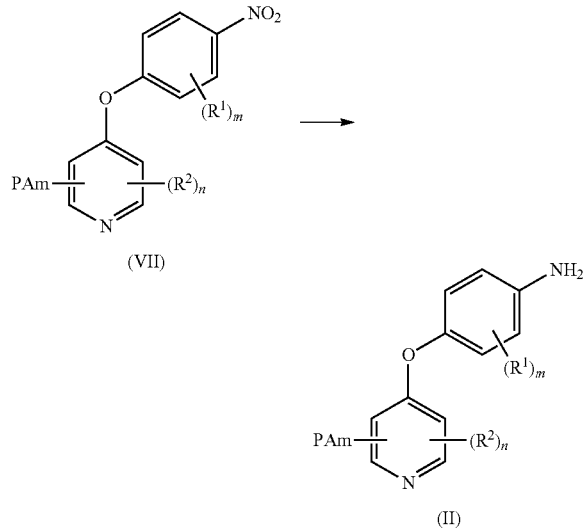

For example, the process of this embodiment can be used to prepare the aniline compound of Formula (IIb) from the compound of Formula (VIIb).

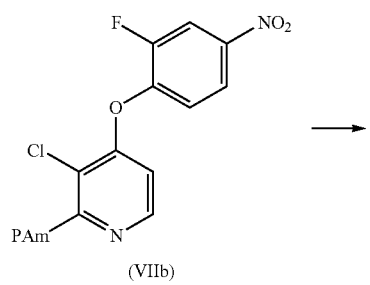

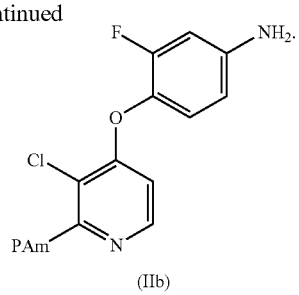

In the process of this embodiment, various solvents, synthesis adjuvants, and reaction conditions can be employed. Examples of suitable solvents include, but are not limited to, polar aprotic solvents such as dimethylformamide, dimethyl sulfoxide, and N-methylpyrrolidinone; etheral solvents such as tetrahydrofuran, 2-methyl tetrahydrofuran, and diethoxymethane; alcohols such as ethanol and isopropanol; hydrocarbons such as toluene, heptane, benzene, and hexanes; halogenated solvents such dichloromethane and 1,2-dichloroethane; acetates such as ethyl acetate, isopropyl acetate, and butyl acetate; other solvents such as acetonitrile and methyl vinyl ketone; or mixtures thereof. The reaction can be conducted in the presence of various synthesis adjuvants including, but not limited to, bases, reductants, transition metals, catalysts, and a hydrogen source. Examples of suitable reductants include, but are not limited to, sodium dithionite sodium sulfide, ammonium sulfide, $FeSO_4$, and sodium borohydride. Examples of suitable transition metals include, but are not limited to, Fe, Pd, Rh, and Ir. Suitable hydrogen sources include hydrogen gas and formic acid. Examples of suitable bases include, but are not limited, inorganic bases such as sodium carbonate, lithium carbonate, and cesium carbonate; and organic bases such as triethylamine and potassium butoxide. The process of the present embodiment can be conducted at temperatures in the range of from about −78° C. to about 200° C., preferably in the range of from −25° C. to about 150° C., and more preferably in the range of from 0° C. to 100° C. The reaction product, the compound of Formula (II), can be separated and purified by methods known in the art. Preferably, the reaction of this embodiment is conducted in a solvent selected from dimethylformamide, dimethyl sulfoxide, N-methylpyrrolidinone, tetrahydrofuran, 2-methyl tetrahydrofuran, diethoxymethane, ethanol, isopropanol, or mixtures thereof. Preferably, the reaction of this embodiment is conducted in the presence of a reductant selected from sodium sulfide, ammonium sulfide, and $FeSO_4$. Preferably, the reaction of this embodiment is conducted in the present of a transition metal selected from Pd or Ni. For example, the process of the present embodiment can be conducted in the presence of ammonium sulfide, nickel such as Raney-Ni, a hydrogen source, and base in a solvent selected from isopropanol, ethanol, tetrahydrofuran, 2-methyl tetrahydrofuran, and mixtures thereof.

In one embodiment, a process is provided for preparing the compound of Formula (VIIb), comprising the steps of reacting 2,3-dichloro-1,4-dihydropyridin-4-ol and 1,2-difluoro-4-nitrobenzene to provide the compound of Formula (IX),

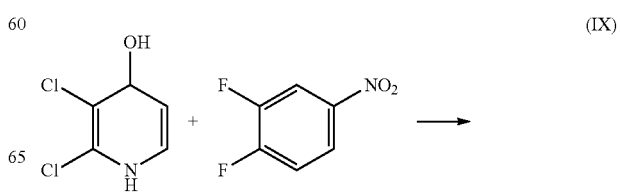

-continued

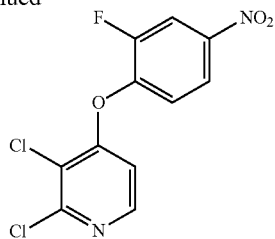

and converting the compound of Formula (IX) to the compound of Formula (II). Suitable solvents, synthesis adjuvants, and reaction conditions are disclosed hereinabove.

In one embodiment, a process is provided for preparing the aniline compound of Formula (II) comprising the steps of: a) reacting a pyridinone compound of Formula (V):

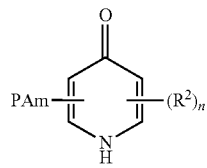
(V)

with a 4-halo-nitrobenzene compound of Formula (VI):

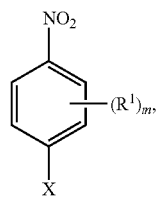
(VI)

wherein X is a halogen and PAm is a protected amine group, to provide a compound of Formula (VII):

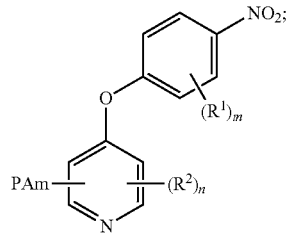
(VII)

and b) converting said compound of Formula (VII) to the aniline compound of Formula (II):

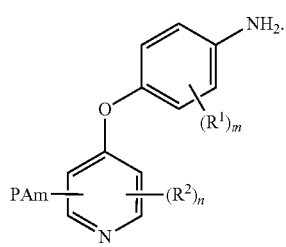
(II)

Preferably, in the process of this embodiment, preferably X is F or Cl. Solvents, synthesis adjuvants, and reaction conditions are disclosed hereinabove.

In one embodiment, a process is provided for preparing the aniline compound of Formula (IIa) comprising the steps of: a) reacting a pyridinone compound of Formula (Va):

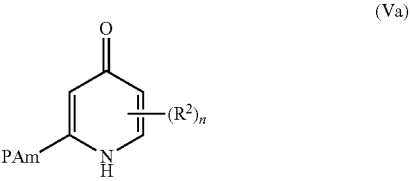
(Va)

with a 4-halo-nitrobenzene compound of Formula (VI), wherein PAm is a protected amine group, to provide a compound of Formula (VIIa):

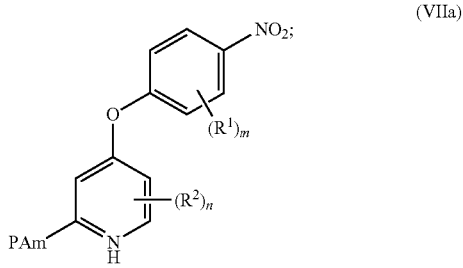
(VIIa)

and b) converting said compound of Formula (VIIa) to the aniline compound of Formula (IIa):

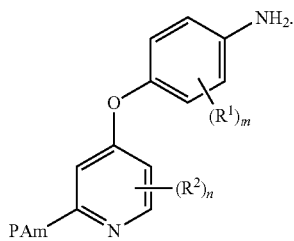
(IIa)

Preferably, in the process of this embodiment, preferably X is F or Cl.

In one embodiment, a process is provided for preparing the aniline compound of Formula (IIb) comprising the steps of: a) reacting a pyridinone compound of Formula (Vb):

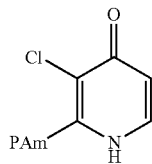
(Vb)

with a 4-halo-nitrobenzene compound of Formula (VI), wherein PAm is a protected amine group, to provide a compound of Formula (VIIb):

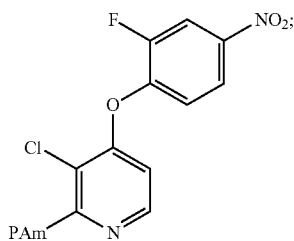

(VIIb)

and b) converting said compound of Formula (VIIb) to the aniline compound of Formula (IIb):

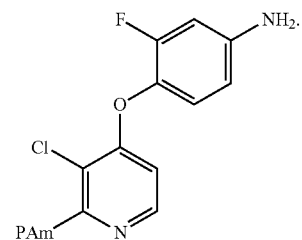

(IIb)

Suitable solvents, synthesis adjuvants, and reaction conditions for step (a) and step (b) are disclosed hereinabove and in the Examples.

EXAMPLES

Abbreviations

BuOAc butyl acetate
DCM dichloromethane
DMF dimethylformamide
EtOH ethanol
Et ethyl
EtOAc ethyl acetate
HPLC high pressure liquid chromatography
hrs hours
LDA lithium diisopropylamine
LOD loss on drying
Me methyl
MeCN acetonitrile
MeOH methanol
MeTHF 2-methyltetrahydrofuran
min minutes
MTBE methyl tert-butyl ether
NaOEt sodium ethoxylate
Ph phenyl
rac-BINAP 2,2'-bis(diphenylphosphino)-1,1'-binaphthylene
THF tetrahydrofuran

Example 1

Preparation of N-(4-(2-amino-3-chloropyridin-4-yloxy)-3-fluorophenyl)-4-ethoxy-1-(4-fluorophenyl)-2-oxo-1,2-dihydropyridine-3-carboxamide

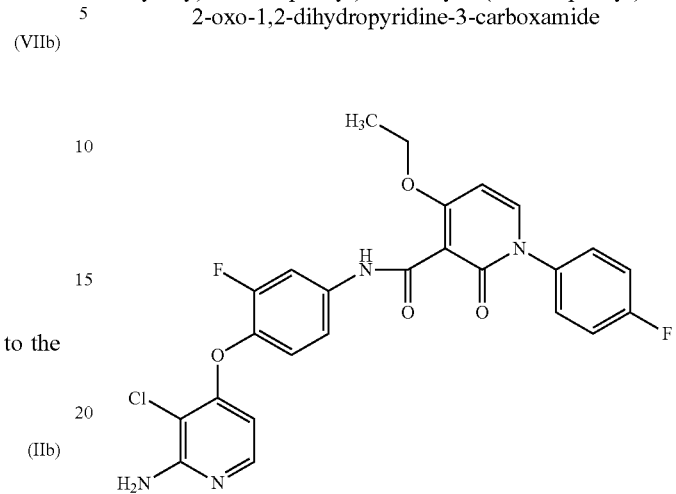

Step 1. Preparation of 3-Chloro-2-(diphenylmethyl-eneamino)pyridin-4(1H)-one

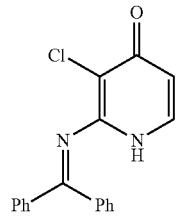

To a reactor, 35 L of MeTHF and 5.0 kg of 2,3 dichloropyridine were charged and agitation started. Next, 0.155 kg of palladium acetate, 0.64 kg of rac-BINAP and 23.0 kg of cesium carbonate were added to the above reaction mixture, followed by the addition of 6.2 kg of benzophenone imine, while maintaining the temperature between 25 and 28° C. The reaction mixture was heated to 80-85° C. and stirred for 24 hours. After the reaction was complete, the reaction mixture was cooled to 25-30° C. The precipitate was filtered off and the solids were washed twice with 20 L of THF. The filtrate was charged back to the equipment and concentrated to minimum volume.

In a separate reactor, 35 L of THF and 10 L of diisopropylamine were charged under nitrogen atmosphere. The mixture was cooled to −20 to −25° C. and 13.3 kg of n-butyllithium were added over a period of 30 min to prepare a lithium diisopropylamide (LDA) solution. Then the mixture was cooled to −75 to −80° C. and the concentrated filtrate, dissolved in 25 L of THF, was slowly dosed to the LDA solution while maintaining the temperature between −75 to −80° C. The reaction mixture was stirred for 2 hours. Afterwards 10.0 L of triisopropylborate were added and the temperature was slowly raised to 20° C. The reaction mixture was stirred for 2 hours at 20° C. Next, the reaction mixture was cooled to 0° C. and 50 L of water were added to the reaction mixture, followed by 30 kg of OXONE™ compound (potassium peroxymonosulfate) while maintaining the temperature between 20-25° C. The reaction mixture was stirred for one hour until the reaction was complete. Then, 270 L of water were added and the reaction mixture was stirred for 12 hours. Next, the slurry was filtered and the solids washed with 40 L of water. The solids were charged back to the reactor and re-slurried in 25 L of ethyl acetate for 30 minutes. After filtration, the solids were washed with 10 L of petroleum ether. The resulting material was removed from the filter and dried for 12 hours at 35-40° C. Yield of 3-Chloro-2-(diphenylmethyleneamino) pyridin-4(1H)-one: off-white solid (6.1 kg; 60% yield).

Step 2. Preparation of 3-Chloro-N-(diphenylmethylene)-4-(2-fluoro-4-nitrophenoxy) pyridin-2-amine

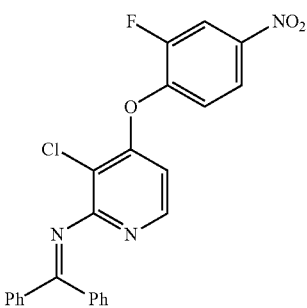 [SMILES: O=[N+]([O-])c1ccc(Oc2ccnc(N=C(c3ccccc3)c3ccccc3)c2Cl)c(F)c1]

To a reactor was added 24 g of 3-chloro-2-(diphenylmethyleneamino) pyridin-4(1H)-one, DMF (100 mL), cesium carbonate (12.7 g; 0.5 eq) and difluoronitrobenzene (9.3 mL; 1.1 eq). The reaction mixture was heated to 95° C. and stirred for three hours. After the reaction was complete, the reaction mixture was poured onto crushed ice and the solids were filtered off and washed with water. The crude solids were charged back to the reactor and dissolved in THF (200 mL). Methanol was added and the mixture was distilled at a constant volume of 350 mL, until THF had been azeotropically removed. Additional methanol (100 mL) was added and the suspension was cooled to room temperature. The solids were filtered and dried under vacuum to yield 3-Chloro-N-(diphenylmethylene)-4-(2-fluoro-4-nitrophenoxy) pyridin-2-amine (23.3 g; 67% yield).

Step 3. Preparation of 4-(4-Amino-2-fluorophenoxy)-3-chloro-N-(diphenylmethylene)pyridin-2-amine

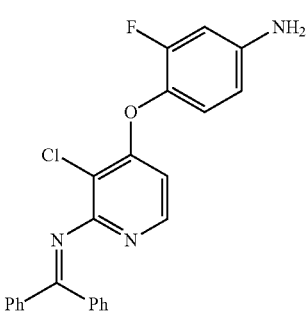 [SMILES: Nc1ccc(Oc2ccnc(N=C(c3ccccc3)c3ccccc3)c2Cl)c(F)c1]

To a reactor was added 10 g of 3-Chloro-N-(diphenylmethylene)-4-(2-fluoro-4-nitrophenoxy)pyridin-2-amine, 1.4 g of Ra-Nickel (type A-5001 from Johnson Matthay) and 100 mL of Me-THF. The reactor was inerted by three nitrogen/hydrogen swings, then pressurized to 25 psig with hydrogen. The reaction mixture was stirred under 25 psig of hydrogen at 25° C. until the hydrogen uptake ceased (1.6 L consumed) and the reaction was judged complete by HPLC. BuOAc (50 mL) was added to the reaction mixture and MeTHF was distilled off under atmospheric pressure until <1% of Me-THF were detected by GC. Maintaining a batch temperature of 90° C., heptane (50 mL) was added over 20 min. The solution was then allowed to cool to room temperature over 8 hrs. The solids were filtered off and the cake was washed with 50 mL heptane. The solid was dried in a vacuum oven at 60° C. for 12 hr to afford 4-(4-Amino-2-fluorophenoxy)-3-chloro-N-(diphenylmethylene)pyridin-2-amine (8.88 g; 95% yield) as a light yellow crystalline solid.

Step 4. Preparation of (4E)-ethyl 2-cyano-5-(dimethylamino)-3-ethoxypenta-2,4-dienoate

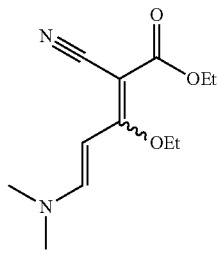 [SMILES: CCOC(=O)C(C#N)=C(/C=C/N(C)C)OCC]

Acetic acid (0.43 kg), ethyl cyanoacetate (16 kg) and triethyl orthoacetate (7.5 kg) were charged to a reactor equipped with a distillation head. The reaction mixture was heated to 110-115° C. until the EtOH was distilled from the reaction mixture. Additional triethyl orthoacetate (4.8 kg) and acetic acid (0.43 kg) were charged and the EtOH distillation was continued. This procedure was repeated until <2% of ethyl cyanoacetate was detected in the reaction mixture by GC. Residual EtOH and triethyl orthoacetate were then removed applying high vacuum to the reaction mixture at 110-115° C. The reaction mass was cooled to 50° C. and N,N'-dimethyl formamide diethylacetal (25.3 kg), DMF and EtOH were added. The mixture was heated to 70° C. for 2 hrs until the reaction was judged complete by HPLC. After cooling to room temperature, DMF (5.6 L) and EtOH (200 proof, 16 L) were added. The mixture was heated to 40° C., until all solids were dissolved. Maintaining the temperature in the range of 35-40° C., water was added. The resulting slurry was cooled to 15-20° C. After 2 hrs, the solids were filtered and the cake washed with 30 L of water, followed by 64 L of petroleum ether. After drying under vacuum, (4E)-ethyl 2-cyano-5-(dimethylamino)-3-ethoxypenta-2,4-dienoate (31.5 kg; 93% yield) was obtained as a brown solid.

Step 5. Preparation of Ethyl 4-ethoxy-2-oxo-1,2-dihydropyridine-3-carboxylate

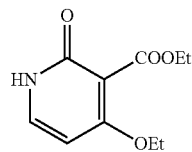 [SMILES: CCOC(=O)c1c(OCC)cc[nH]c1=O]

(4E)-Ethyl 2-cyano-5-(dimethylamino)-3-ethoxypenta-2,4-dienoate (20 kg) and acetic acid (126 L) were charged to a reactor and heated to 100° C. for 3 hrs until the reaction was complete as characterized by HPLC. The reaction mass was cooled to 55° C. and acetic acid was removed by vacuum distillation at 65-75° C. After distillation, the mixture was cooled to room temperature and water (3 L) was added. The pH of the mixture was adjusted to 8 by addition of 100 L of a 30% sodium carbonate solution. The solids were filtered off and washed with 10 L of water. The combined aqueous layers were extracted three times with DCM (100 L). The combined DCM layers were washed with brine, then dried over sodium sulfate and concentrated to dryness. Ethyl acetate was added to the concentrate. The mixture was heated to 40° C. and then cooled to 25° C. The solids were filtered off, washed with petroleum ether and dried at room temperature for 12 hrs to yield ethyl 4-ethoxy-2-oxo-1,2-dihydropyridine-3-carboxylate (10.3 kg; 58.5% yield).

Step 6. Preparation of Ethyl 4-ethoxy-1-(4-fluorophenyl)-2-oxo-1,2-dihydropyridine-3-carboxylate

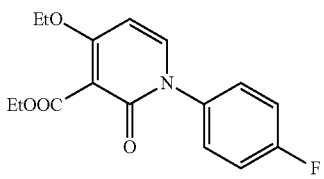 [SMILES: CCOC(=O)c1c(OCC)ccn(-c2ccc(F)cc2)c1=O]

DMF (9 L) and cesium carbonate (3.1 kg) were charged under nitrogen to a reactor and stirred for 10 min at room temperature. To this mixture, a solution of 8-hydroxyquinoline (0.275 kg) in DMF (1 L), copper iodide (0.27 kg) and 1-fluoro-4-iodobenzene (1.576 kg) were added under nitrogen. Then, ethyl 4-ethoxy-2-oxo-1,2-dihydropyridine-3-carboxylate (1 kg) was added and the reaction mixture was heated to 100° C. for 20 hrs under nitrogen. After completion of the reaction, the mixture was filtered through celite. To the filtrate, water (100 L) was added and the mixture was extracted three times with DCM (25 L). The combined DCM layers were washed two times with water (20 L), two times with 1.5 N HCl (5 L), and one time with brine (10 L), and then dried over sodium sulfate and concentrated to dryness. Petroleum ether (5 L) was added to the concentrate and the resulting slurry was stirred for 30 min. The solids were filtered and dried at room temperature in vacuum to give 1.1 kg crude ethyl 4-ethoxy-1-(4-fluorophenyl)-2-oxo-1,2-dihydropyridine-3-carboxylate.

Step 7. Preparation of Carboxylic Acid Compound: 4-Ethoxy-1-(4-fluorophenyl)-2-oxo-1,2-dihydropyridine-3-carboxylic acid

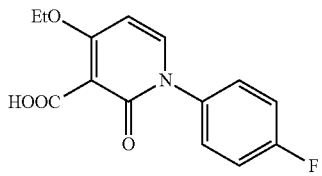 [SMILES: CCOc1ccn(-c2ccc(F)cc2)c(=O)c1C(=O)O]

At room temperature, 2.75 N HCl (7.7 L) was added to a solution of crude ethyl 4-ethoxy-1-(4-fluorophenyl)-2-oxo-1,2-dihydropyridine-3-carboxylate (1.1 kg) in EtOH (3.85 L). The mixture was heated for 10 hrs to 60-64° C. Next, the mixture was cooled to 50-54° C. and methanol was removed by vacuum distillation. The mixture was cooled to 20-25° C. and the pH was adjusted to 8.0 to 8.5 by addition of 30% sodium carbonate solution (8.5 L). The phases were separated and the aqueous layer was washed three times with DCM (4 L). Next, charcoal (0.7 kg) was charged to the aqueous layer and the layer was filtered through a celite bed. To the filtrate was added 1.5 N HCl until the pH had reached 2.0. The resulted slurry was stirred for 20 min at room temperature. The solids were filtered off, washed with water (15 L) and dried under vacuum at 50-55° C. until the loss on drying was less than 5 wt %. The crude product was suspended in ethyl acetate (5 L) and slurried for 15 min at 40° C. After cooling to room temperature, the solids were filtered off, washed with ethyl acetate (1 L) and dried at 40-45° C. under vacuum for 10 hrs to yield 4-ethoxy-1-(4-fluorophenyl)-2-oxo-1,2-dihydropyridine-3-carboxylic acid (0.76 kg; 58% yield for Steps 6 and 7).

Step 8. Preparation of N-(4-(3-chloro-2-(diphenylmethyleneamino)pyridin-4-yloxy)-3-fluorophenyl)-4-ethoxy-1-(4-fluorophenyl)-2-oxo-1,2-dihydropyridine-3-carboxamide

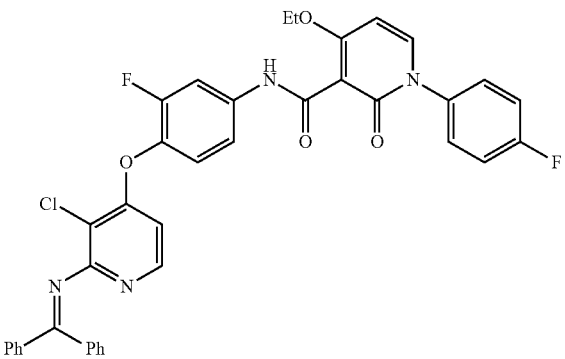 [SMILES: CCOc1ccn(-c2ccc(F)cc2)c(=O)c1C(=O)Nc1ccc(Oc2ccnc(N=C(c3ccccc3)c3ccccc3)c2Cl)c(F)c1]

4-Ethoxy-1-(4-fluorophenyl)-2-oxo-1,2-dihydropyridine-3-carboxylic acid (1.20 equiv; 79.62 g), DCM (500.00 mL), and oxalyl chloride (23.88 mL) were added to a ChemGlass reactor at 25° C. DMF (20.00 mL) was added over a period of approximately 20 min and the solution was allowed to stir at 20° C. for 30 min. The resulting acid chloride solution was cooled to −5° C.

Into a separate reactor, 4-(4-amino-2-fluorophenoxy)-3-chloro-N-(diphenylmethylene)pyridin-2-amine (1.00 equiv; 100 g), DCM (500 mL), and sodium 2-ethylhexanoate (95.45 g) were charged and the resulting mixture (aniline solution) was cooled to −5° C.

The pre-cooled acid chloride solution was then added to the aniline solution keeping the batch temperature below 5° C. The mixture was allowed to stir at −5° C. for 3 hrs. After HPLC indicated the reaction was complete, the reaction was quenched with methanol (29.06 mL). DCM (500 mL), aqueous sodium bicarbonate (500 mL), and water (500 mL) were added to the solution and the solution was allowed to warm to 25° C. with stirring. The layers were separated and the aqueous layer was discarded. The DCM layer was washed with sodium bicarbonate (500 mL) and water (500 mL).

Diethoxymethane (total of 1500 mL) was added to the DCM layer and DCM was distilled off until the batch temp reached 85° C., keeping the volume constant at 10 L/kg. After GC analysis of the reaction mixture showed a diethoxymethane/DCM ratio of 99:1, the distillation was stopped and the mixture was cooled to 25° C. The precipitate was filtered off and the cake was washed with diethoxymethane (1.00 L), then methyl t-butyl ether (500 mL). The solids was dried in a vacuum oven at 60° C. for 12 h to afford N-(4-(3-chloro-2-(diphenylmethyleneamino)pyridin-4-yloxy)-3-fluorophenyl)-4-ethoxy-1-(4-fluorophenyl)-2-oxo-1,2-dihydropyridine-3-carboxamide (0.97 equiv; 157.02 g; 96.90% yield) as a white solid.

Step 9. Preparation of N-(4-(2-amino-3-chloropyridin-4-yloxy)-3-fluorophenyl)-4-ethoxy-1-(4-fluorophenyl)-2-oxo-1,2-dihydropyridine-3-carboxamide

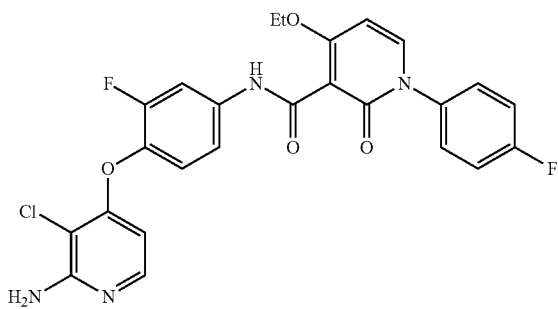 [SMILES: CCOc1ccn(-c2ccc(F)cc2)c(=O)c1C(=O)Nc1ccc(Oc2ccnc(N)c2Cl)c(F)c1]

To a 250 mL vessel, N-(4-(3-chloro-2-(diphenylmethyleneamino)pyridin-4-yloxy)-3-fluorophenyl)-4-ethoxy-1-(4-fluorophenyl)-2-oxo-1,2-dihydropyridine-3-carboxamide (100.0 g, 147.7 mmoles, 1.0 eq) and methanol (900 mL) were charged. The white slurry was cooled to 10° C. and concentrated HCl (16.3 g, 163.3 mmoles, 1.105 eq) was added, maintaining the reaction temperature below 10° C. The reaction mixture was held at 10° C. for approximately 2.5 h, until HPLC indicated 0.5 relative area percent of starting material. Water (500 mL) and MTBE (500 mL) were added and the reaction mixture was warmed to 20° C. Next, 1N NaOH (184.08 g, 177.0 mL, 177 mmoles, 1.20 eq), was added dropwise over 20 minutes while maintaining the temperature between 15 and 20° C. The resulting slurry was cooled to 10° C. and aged for at least 10 minutes. The precipitate was filtered off, and the cake washed with water (2×350 mL), followed by a mixture of methanol:MTBE (10:90) (1×300 mL). Next, the cake was dried in a vacuum oven at 50-60° C. until LOD analysis indicated less than 1 wt % of volatiles. N-(4-(2-amino-3-chloropyridin-4-yloxy)-3-fluorophenyl)-4-ethoxy-1-(4-fluorophenyl)-2-oxo-1,2-dihydropyridine-3-carboxamide: 79.5 g (95% yield with 98.1 AP and 99.4 wt % potency). The resulting product (35.0 g) was subsequently re-crystallized from THF (367.2 mL)/EtOH (200 proof, 244.8 mL)/n-heptane (350 mL) to obtain N-(4-(2-amino-3-chloropyridin-4-yloxy)-3-fluorophenyl)-4-ethoxy-1-(4-fluorophenyl)-2-oxo-1,2-dihydropyridine-3-carboxamide (30.8 g) in 88% yield with >99.9 AP and 99.7 wt % potency.

Comparative Example 2

Preparation of N-(4-(2-amino-3-chloropyridin-4-yloxy)-3-fluorophenyl)-4-ethoxy-1-(4-fluorophenyl)-2-oxo-1,2-dihydropyridine-3-carboxamide by Process Disclosed in US 2008/0114033 A1

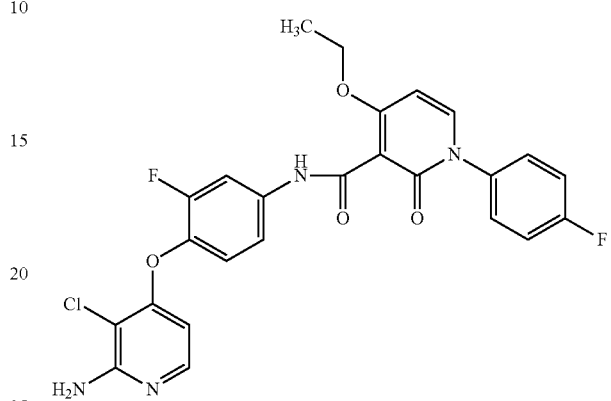

Step 1. Preparation of 3,4-Dichloropicolinic acid

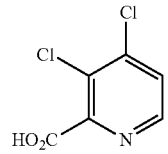 [SMILES: O=C(O)c1nccc(Cl)c1Cl]

As described previously by Marzi, E. et al. (*Eur. J. Org. Chem.* 2001, 1371-1376), 2,2,6,6-tetramethylpiperidine (8.84 mL, 52 mmol, Aldrich) in 50 mL of ether at 0° C. was charged with n-BuLi (33 mL, 52 mmol, Aldrich, 1.6 M hexanes). After stirring at 0° C. for 30 min, the solution was cooled to −78° C. and charged with a solution of 3,4-dichloropyridine (7.0 g, 47 mmol, Matrix) in 5 mL of ether. After stirring at −78° C. for 2 h, carbon dioxide (dry ice) was bubbled into the reaction mixture via cannula at which time the solution became heterogeneous. After bubbling carbon dioxide into the reaction at −78° C. for 10 min, the cooling bath was removed and the reaction mixture was allowed to warm to room temperature, while continuing to bubble $CO_2$ through the solution. The reaction was quenched with saturated aqueous ammonium chloride solution (~50 mL) and stirred at rt under an atmosphere of air for 5 min. The reaction mixture was diluted with water (~150 mL) and extracted with ethyl acetate (2×75 mL) to remove any remaining starting material. The aqueous layer was acidified to pH 1-2 with 1N aqueous HCl solution and extracted with ethyl acetate (2×100 mL). The organic phase was dried over anhydrous magnesium sulfate and concentrated in vacuo to give 3,4-dichloropicolinic acid (3.5 g, 39%) as a yellow solid. $^1$H NMR (DMSO-$d_6$) δ 8.53 (d, 1H, J=5.2 Hz), 7.90 (d, 1H, J=5.2 Hz); MS (ESI$^+$) m/z 192.08 (M+H)$^+$.

Step 2. Preparation of 3,4-Dichloropicolinamide

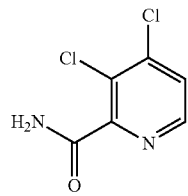 [SMILES: NC(=O)c1nccc(Cl)c1Cl]

A solution of 3,4-dichloropicolinic acid (3.5 g, 18 mmol) in excess thionyl chloride (10 mL, Aldrich ReagentPlus 99.5%) was stirred at 80° C. for 1 h. After cooling to room temperature, the reaction mixture was concentrated in vacuo to remove excess thionyl chloride and then suspended in ether (50 mL). The ethereal acid chloride solution was added to ammonium hydroxide (50 mL) at 0° C. The product was collected by vacuum filtration, washed with water, and then triturated with ether to give 3,4-dichloropicolinamide (2.6 g, 76%) as a beige solid. m.p. 174-175° C.; $^1$H NMR (400 MHz, DMSO-$d_6$) δ 8.50 (d, 1H, J=5.2 Hz), 8.12 (br s, 1H), 7.83 (d, 1H, J=5.2 Hz), 7.82 (br s, 1H); $^{13}$C NMR (100 MHz, DMSO-$d_6$) δ 166.2, 154.2, 147.9, 142.3, 126.1, 126.0; MS (ESI$^+$) m/z 191.10 (M+H)$^+$.

Step 3. Preparation of 4-(4-Amino-2-fluorophenoxy)-3-chloropicolinamide

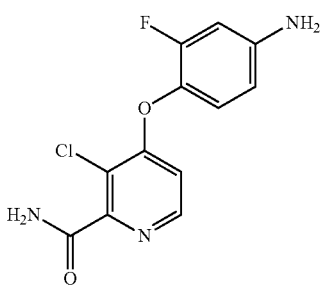 [SMILES: NC(=O)c1nccc(Oc2ccc(N)cc2F)c1Cl]

To a solution of 4-amino-2-fluorophenol (9.3 g, 73 mmol, 3B Medical Systems, 3B3290) in DMF (100 mL) was added potassium tert-butoxide (8.8 g, 79 mmol). After stirring at rt for 30 min, 3,4-dichloropicolinamide (10 g, 52 mmol) was added. The reaction mixture was stirred at 50° C. for 2.5 h. After cooling the reaction to rt, the mixture was diluted with 400 mL of ethyl acetate and washed with saturated aqueous sodium bicarbonate solution (400 mL). The aqueous layer was back-extracted with 300 mL ethyl acetate. The combined organic phases were washed with 10% aqueous lithium chloride solution, dried over anhydrous sodium sulfate, and concentrated in vacuo. The resulting brown solid was suspended in ethyl acetate, filtered and washed with ether to give the product as a tan solid (7.4 g). The filtrate was concentrated in vacuo and then purified by flash chromatography on silica gel (2% methanol/ethyl acetate). The resulting brown solid was triturated with ether to give an additional 4.3 g of 4-(4-amino-2-fluorophenoxy)-3-chloropicolinamide (79% combined yield) as a pale tan solid. m.p. 217-218° C.; $^1$H NMR (400 MHz, CD$_3$OD) δ 8.29 (d, 1H, J=5.6 Hz), 7.00 (t, 1H, J=8.8 Hz), 6.79 (d, 1H, J=5.6 Hz), 6.63-6.55 (m, 2H); MS (ESI$^+$) m/z 282.21 (M+H)$^+$.

Step 4. Preparation of 4-Iodo-2-methoxynicotinaldehyde

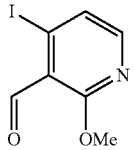 [SMILES: COc1nccc(I)c1C=O]

To a solution of diisopropylamine (260 g, 2.57 mol) in anhydrous THF (6.5 L) at −30 to −40° C. under a blanket of N$_2$ was added n-BuLi (156 g, 2.45 mol) dropwise via cannula. The resulting solution was allowed to warm to 0° C. and stirred at this temperature for 35 min. The solution was then cooled to −78° C. and 2-fluoropyridine (250 g, 2.57 mol, Alfa) was added dropwise. The reaction mixture was stirred at −78° C. for 2 h. This mixture was then added via cannula to a solution of iodine (654 g, 2.57 mol) in anhydrous THF (1.96 L) at −20° C. under N$_2$. After the reaction was complete, the mixture was quenched with ice water and extracted with EtOAc. The organic layer was washed with sodium thiosulfate followed by water and brine. The organics were then dried (Na$_2$SO$_4$) and concentrated in vacuo to give 2-fluoro-3-iodopyridine (450 g, 78%) as a solid.

To a solution of diisopropylamine (345 mL, 249 g, 2.46 mol) in anhydrous THF (5 L) at −8 to −10° C. under a blanket of N$_2$ was added n-BuLi (880 mL, 158 g, 2.46 mol) dropwise via cannula. The mixture was stirred at −10° C. for 30 min, cooled to −78° C. and treated with a solution of 2-fluoro-3-iodopyridine (500 g, 2.24 mol) in dry THF (2 L) dropwise. After the addition, the reaction mixture was warmed to −60° C. and this temperature was maintained for 2 h. The mixture was then cooled to −78° C., treated with ethyl formate (183 g, 2.47 mol) dropwise, followed by sodium methoxide (149 g, 2.75 mol) in MeOH (1.5 L) and warmed to ambient temperature. The reaction mixture was quenched with ice water and extracted with EtOAc. The layers were separated and the organic phase was washed with water and brine, dried (Na$_2$SO$_4$) and concentrated in vacuo. The residue was purified by flash chromatography on silica gel to afford 4-iodo-2-methoxynicotinaldehyde (380 g, 64%) as a solid.

Step 5. Preparation of 4-Iodo-2-oxo-1,2-dihydropyridine-3-carbaldehyde

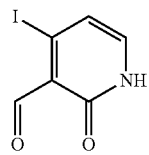

4-Iodo-2-methoxynicotinaldehyde (25 g, 95 mmol) and sodium iodide (31.0 g, 285 mmol, Aldrich) were stirred together in 500 mL of acetonitrile. To this solution was added chlorotrimethylsilane (36.0 mL, 285 mmol, Aldrich >99%) dropwise over 15 minutes. The reaction mixture was stirred for 2 h at room temperature and then concentrated under vacuum. The product was suspended in ethyl acetate, water, and saturated aqueous sodium bicarbonate, then filtered to give a dark brown solid. This solid was triturated with acetonitrile to yield 4-iodo-2-oxo-1,2-dihydropyridine-3-carbaldehyde (21.3 g, 90%) as a yellow solid (mixture of tautomers). MS (ESI+) m/z 250.04 (M+H)+.

Step 6. Preparation of 1-(4-Fluorophenyl)-4-iodo-2-oxo-1,2-dihydropyridine-3-carbaldehyde

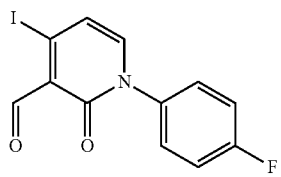 [SMILES: O=Cc1c(I)ccn(-c2ccc(F)cc2)c1=O]

4-Iodo-2-oxo-1,2-dihydropyridine-3-carbaldehyde (16.0 g, 64.3 mmol), 4-fluorophenylboronic acid (26.8 g, 193 mmol, Aldrich), copper(II) acetate (23.4 g, 129 mmol, Aldrich), and myristic acid (58.7 g, 257 mmol, Aldrich) were stirred together in 800 mL of toluene. To this solution was added 2,6-lutidine (60 mL, 514 mmol, Aldrich) and the reaction was stirred vigorously for 1 day. An additional 5 g of 4-fluorophenylboronic acid was added and the reaction was stirred vigorously for an additional 3 days. The reaction mixture was concentrated in vacuo and the resulting material was suspended in 10% methanol/ethyl acetate. Celite® was added and the mixture was stirred for 5 minutes. Next the mixture was filtered through a plug of Celite®, concentrated in vacuo, and the resulting material was suspended in ethyl acetate and water. The mixture was filtered through Celite® again to remove additional copper that had precipitated out, washing well with ethyl acetate. The filtrate was washed with 1N aqueous HCl, dried over sodium sulfate, filtered, and concentrated under vacuum. The resulting solid was triturated with ethyl acetate to yield 9.25 g (42%) of 1-(4-fluorophenyl)-4-iodo-2-oxo-1,2-dihydropyridine-3-carbaldehyde as a yellow solid. The filtrate was concentrated in vacuo and the remaining solid was triturated again with ethyl acetate to yield an additional 5.75 g (68% total yield) of the desired product as a yellow solid. $^1$H NMR (DMSO-$d_6$) δ 9.57 (s, 1H), 7.68 (d, 1H, J=7.2 Hz), 7.58-7.54 (m, 2H), 7.40 (t, 2H, J=8.8 Hz), 7.02 (d, 1H, J=7.2 Hz); MS (ESI+) m/z 344.13 (M+H)+.

Step 7. Preparation of 1-(4-Fluorophenyl)-4-iodo-2-oxo-1,2-dihydropyridine-3-carboxylic acid

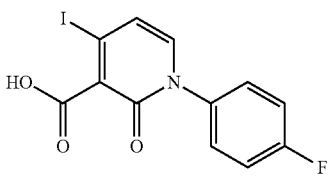 [SMILES: O=C(O)c1c(I)ccn(-c2ccc(F)cc2)c1=O]

1-(4-Fluorophenyl)-4-iodo-2-oxo-1,2-dihydropyridine-3-carbaldehyde (10.0 g, 29.2 mmol) and sodium phosphate monobasic (10.1 g, 73 mmol, Aldrich) were stirred vigorously in 35 mL each of THF, tert-butanol, and water at 0° C. 2-Methyl-2-butene (45.2 mL, 2.0 M in THF, Aldrich) was added to the reaction mixture, followed by sodium chlorite (6.06 g, 67.1 mmol, Aldrich). The ice bath was removed and the reaction mixture was warmed to room temperature, stirring very rapidly. After a few minutes the desired product began precipitating out of solution. Stirring was continued for 1 h, then 20 mL of 1N aqueous HCl was added, and stirring was continued for another 5 minutes. The desired product was filtered off, then washed with water, ethyl acetate, and ether. The filtrate was taken and the layers were separated. The aqueous layer was extracted with ethyl acetate. The combined organic layers were dried over magnesium sulfate, filtered, and concentrated in vacuo. The resulting solid was suspended in ethyl acetate, filtered, and washed with ethyl acetate and ether to yield additional desired product. The pale yellow solids were combined to yield 8.22 g (78%) of 1-(4-fluorophenyl)-4-iodo-2-oxo-1,2-dihydropyridine-3-carboxylic acid (92% pure, 8% starting material remaining). This material was dissolved in a minimal amount of 1N aqueous NaOH. Ethyl acetate was added and the mixture was stirred vigorously for 5 minutes. The layers were separated, and the aqueous layer was extracted with ethyl acetate. The aqueous layer was acidified, with stirring, using concentrated HCl to pH 1. The pale yellow solid that precipitated out of solution was collected, washed with water, ethyl acetate, diethyl ether and then dried under vacuum to afford 7.33 g (70%) of 1-(4-fluorophenyl)-4-iodo-2-oxo-1,2-dihydropyridine-3-carboxylic acid (95.4% pure by HPLC). $^1$H NMR (DMSO-$d_6$) δ 13.53 (s, 1H), 7.52-7.49 (m, 3H), 7.38 (t, 2H, J=8.8 Hz), 6.81 (d, 1H, J=7.2 Hz); MS (ESI+) m/z 360.14 (M+H)+.

Step 8. Preparation of 3-Chloro-4-(2-fluoro-4-(1-(4-fluorophenyl)-4-iodo-2-oxo-1,2-dihydropyridine-3-carboxamido)phenoxy)picolinamide

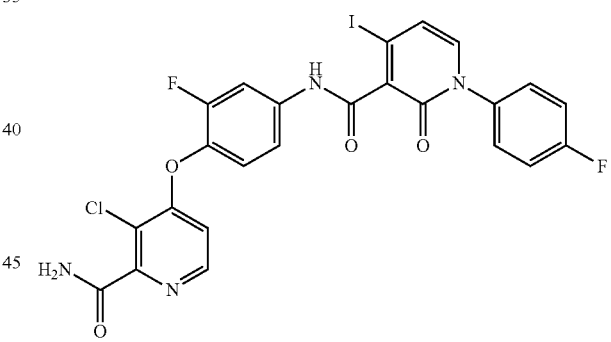

To a suspension of 1-(4-fluorophenyl)-4-iodo-2-oxo-1,2-dihydropyridine-3-carboxylic acid (36.3 g, 101 mmol) in a mixture of 500 mL of DCM and 0.25 mL of DMF at 0° C. was added oxalyl chloride (38.5 g, 26.5 ml, 303 mmol) dropwise over 0.5 h. The reaction mixture became homogeneous after stirring at room temperature for 2 h and was then concentrated in vacuo. The resulting residue was resuspended in DCM (200 ml) and the mixture was again concentrated in vacuo to remove any remaining oxalyl chloride (performed twice). The crude acid chloride compound was then dried under high vacuum for 0.5 h. While the carboxylic acid chloride compound was drying, 4-(4-amino-2-fluorophenoxy)-3-chloropicolinamide (22.8 g, 81 mmol) was dissolved in THF (200 mL) and DMF (50 mL). The solution was cooled to 0° C. and pyridine (12.8 g, 162 mmol) was added. A solution of the carboxylic acid chloride compound in 250 mL of DCM was then added to the reaction mixture dropwise over 40 minutes. The cooling bath was removed and the reaction mixture was stirred at room temperature for 0.5 h before being quenched with water (50 mL). The volatiles were removed under reduced pressure until the volume was reduced to approximately 100 mL. The contents of the flask were dissolved in EtOAc (1 L) and the solution was washed sequentially with 1N HCl (2×200 mL), saturated aqueous NaHCO₃ (2×200 mL), 10% aq. LiCl solution (3×200 mL) and saturated aq. NaCl solution (200 mL). The organic phase was dried over anhydrous sodium sulfate, filtered through a pad of silica gel (washed with 500 mL EtOAc) and the filtrate was concentrated in vacuo. The crude product was triturated with MeOH (100 mL) and the solid was filtered, washed with MeOH (10 mL) and collected. The filtrate was concentrated in vacuo and the trituration process was repeated. The two batches of solid were combined, suspended in EtOH (100 mL) and concentrated in vacuo. The solid was again suspended in EtOH (50 mL) and concentrated in vacuo. The resulting solid dried overnight under high vacuum to afford 3-Chloro-4-(2-fluoro-4-(1-(4-fluorophenyl)-4-iodo-2-oxo-1,2-dihydropyridine-3-carboxamido) phenoxy)picolinamide (40.3 g, 80%) as an off-white solid. $^1$H NMR (400 MHz, CD$_3$OD) δ 8.34 (d, 1H, J=5.6 Hz), 7.92 (dd, 1H, J=12.4, 2.4 Hz), 7.51-7.47 (m, 4H), 7.37-7.29 (m, 3H), 6.99 (d, 1H, J=7.2 Hz), 6.86 (d, 1H, J=5.6 Hz); MS (ESI$^+$) m/z 623.08 (M+H)$^+$.

Step 9. Preparation of 3-Chloro-4-(4-(4-ethoxy-1-(4-fluorophenyl)-2-oxo-1,2-dihydropyridine-3-carboxamido)-2-fluorophenoxy)picolinamide

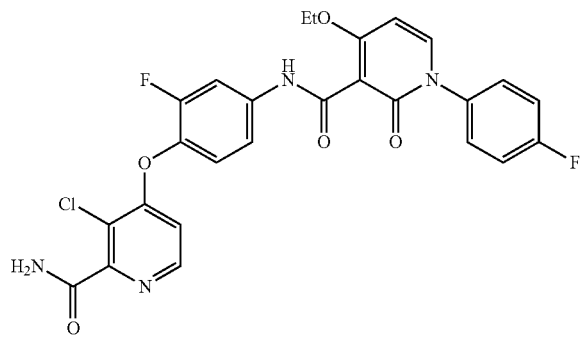 [SMILES: CCOc1ccn(-c2ccc(F)cc2)c(=O)c1C(=O)Nc1ccc(Oc2ccnc(C(N)=O)c2Cl)c(F)c1]

To a suspension of NaH (1.87 g, 77.9 mmol) in THF (26 mL) under nitrogen was slowly added EtOH (80 mL, Aldrich>99.5%, 200 proof) and the resulting homogeneous solution was stirred for 10 minutes. The sodium ethoxide solution was then added to a mixture of 3-Chloro-4-(2-fluoro-4-(1-(4-fluorophenyl)-4-iodo-2-oxo-1,2-dihydropyridine-3-carboxamido)phenoxy)picolinamide (37.3 g, 59.9 mmol) in THF (100 mL) and EtOH (46 mL), and the resulting mixture was stirred at room temperature for 1 h before being concentrated in vacuo. The residue was suspended in water (500 mL) and the mixture was sonicated and stirred for about 1 h at room temperature until the remaining solid became a filterable powder. The resulting powder was collected, triturated with ethyl ether (50 mL) and dried under high vacuum for 48 h to afford 3-Chloro-4-(4-(4-ethoxy-1-(4-fluorophenyl)-2-oxo-1,2-dihydropyridine-3-carboxamido)-2-fluorophenoxy)picolinamide (30.8 g, 95%) as a pale yellow solid. $^1$H NMR (400 MHz, CD$_3$OD) δ 8.34 (d, 1H, J=5.6 Hz), 7.94 (dd, 1H, J=12.4, 2.4 Hz), 7.80 (d, 1H, J=8 Hz), 7.48-7.46 (m, 3H), 7.31-7.28 (m, 3H), 6.86 (d, 1H, J=5.6 Hz), 6.61 (d, 1H, J=7.2 Hz), 4.34 (q, 2H, J=7.2 Hz), 1.45 (t, 3H, J=7.2 Hz); MS (ESI$^+$) m/z 541.11 (M+H)$^+$.

Step 10. Preparation of N-(4-(2-Amino-3-chloropyridin-4-yloxy)-3-fluorophenyl)-4-ethoxy-1-(4-fluorophenyl)-2-oxo-1,2-dihydropyridine-3-carboxamide To a mixture of 3-chloro-4-(4-(4-ethoxy-1-(4-fluorophenyl)-2-oxo-1,2-dihydropyridine-3-carboxamido)-2-fluorophenoxy)picolinamide (13.9 g, 25.7 mmol) in EtOAc (200 mL), MeCN (200 mL), and water (100 mL) at 0° C. was added iodobenzene diacetate (9.93 g, 30.8 mmol). The reaction mixture was slowly warmed to room temperature and stirred for 1 h. The resulting precipitate was filtered and washed with ethyl acetate. The combined filtrates were washed with saturated aqueous sodium bicarbonate solution and the organic phase was dried over anhydrous sodium sulfate and concentrated in vacuo. This residue and the original precipitate were combined and purified by flash chromatography (SiO₂, 0-2% methanol/chloroform gradient elution) to give N-(4-(2-Amino-3-chloropyridin-4-yloxy)-3-fluorophenyl)-4-ethoxy-1-(4-fluorophenyl)-2-oxo-1,2-dihydropyridine-3-carboxamide (9.8 g, 74%) as an off-white solid. $^1$H NMR (DMSO-d₆) δ 10.57 (s, 1H), 7.83-7.79 (m, 2H), 7.67 (d, 1H, J=5.6 Hz), 7.41-7.38 (m, 3H), 7.36-7.22 (m, 3H), 6.44 (d, 1H, J=7.6 Hz), 6.36 (br s, 2H), 5.86 (d, 1H, J=6.0 Hz), 4.18 (q, 2H, J =7.2 Hz), 1.23 (t, 3H, J=7.2 Hz); MS (ESI$^+$) m/z 513.09 (M+H)$^+$.

TABLE 2

Comparison of Processes of Example 1 and Comparative Example 2

| Process | Example 1 (yield) | Comparative Example 2 (yield) |
| --- | --- | --- |
| Steps 1 to 3 to prepare aniline compound | 38% | 23% |
| Steps 4-7 to prepare acid compound | 32% | 21% |
| Coupling of acid and aniline compounds to prepare pyridinone compound | 81% (steps 8-9) | 56% (steps 8-10) |
| Overall yield (based on acid compound as limiting reagent) | 26% | 12% |

Example 3

N-(4-(2-Amino-3-chloropyridin-4-yloxy)-3-fluorophenyl)-5-(4-fluorophenyl)-4-oxo-1,4-dihydropyridine-3-carboxamide

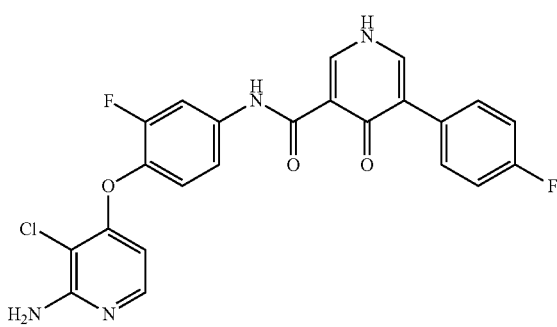

(3)

Preparation 3A: 3-Chloro-N-(diphenylmethylene)pyridin-2-amine

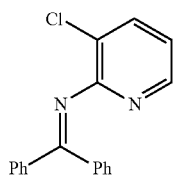

(3A)

2,3-Dichloropyridine (105.00 g, 710 mmol), Pd(OAc)$_2$ (3.98 g, 17.74 mmol), rac-BINAP (16.57 g, 26.61 mmol), cesium carbonate (346.76 g, 1065 mmol), THF (1.05 L), and benzophenone imine (124.67 mL, 745 mmol) were added to a 2 L Chem-Glass Reactor fitted with a mechanical stirrer and reflux condenser. The mixture was heated to reflux with stirring for 18 h. The material was filtered, washed with THF (100 mL). The resulting filtrate was concentrated in vacuo to ⅓ volume and used without further purification. $^1$H NMR (CDCl$_3$) δ 6.79 (dd, 1 H, J=4.6, 7.6 Hz), 7.19-7.60 (m, 9 H), 7.79-7.95 (m, 2 H), 8.16 (dd, 1 H, J=1.5, 5.1 Hz); MS (ESI$^+$) m/z 293.1 (M+H)$^+$.

Preparation 3B: 3-Chloro-2-(diphenylmethyleneamino)pyridin-4(1H)-one

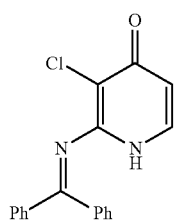

(3B)

To a 4-L Chemglass reactor (fitted with addition funnel, nitrogen blanket) was added: crude 3-chloro-N-(diphenylmethylene)pyridin-2-amine and triisopropyl borate (196.38 mL, 852 mmol). The resulting solution was the cooled to 0° C. In a separate reactor was added diisopropylamine (169.78 mL, 1207 mmol) and THF (1.05 L). This solution was cooled to 0° C. and n-butyl lithium (683.22 mL, 923 mmol) was added slowly. After stirring at 0° C., this solution was added slowly to the first solution. The reaction mixture was stirred for 30 min without the cooling bath (HPLC indicated consumption of starting material). Water (1.05 L) was added to the mixture, followed by the addition of sodium percarbonate (336.34 g, 1065 mmol) in one portion. This mixture was allowed to stir at 20° C. for 1 h. A saturated solution of NaHSO$_3$ (~1 L) was added slowly. The aqueous layer was removed and DMF (840.00 mL) was added to the organic layer and the THF was distilled off (solvent swap from THF to DMF). The DMF was used without further purification. $^1$H NMR (CDCl$_3$) δ 6.02 (d, 1 H, J=7.1 Hz), 7.10 (d, 1 H, J=7.1 Hz), 7.20-7.80 (m, 10 H); MS (ESI$^+$) m/z 309.07 (M+H)$^+$.

Preparation 3C: 3-Chloro-N-(diphenylmethylene)-4-(2-fluoro-4-nitrophenoxy) pyridin-2-amine

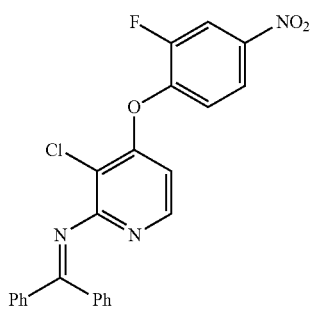

(3C)

To a 2-L Chem-Glass reactor was added the crude 3-chloro-2-(diphenylmethyleneamino)pyridin-4(1H)-one (from above, now in DMF) and cesium carbonate (300.52 g, 923 mmol) followed by the addition of 3,4-difluoronitrobenzene (118.15 mL, 1065 mmol). The mixture was heated to approximately 90° C. with stirring for 2 h. The mixture was cooled to 25° C. with stirring for 10 min. To this solution was added water (1 L). The mixture was extracted with EtOAc (1 L) and the aqueous phase was discarded. The organics were concentrated to afford an oil. The oil was dissolved into EtOH (200 mL) (heating sometimes required). After the solution was allowed to stand at 25° C. for 4 h, a solid was collected by filtration to afford 3-chloro-N-(diphenylmethylene)-4-(2-fluoro-4-nitrophenoxy)pyridin-2-amine (104.00 g; 32.73% yield) as a yellow solid. $^1$H NMR (CDCl$_3$) δ 6.52 (d, 1 H, J=5.6 Hz), 6.80 (dd, 1 H, J=8.1, 9.1 Hz), 7.21-7.60 (m, 8 H), 7.78-7.95 (m, 2 H), 8.00 (m, 1 H), 8.11 (dd, 1 H, J=2.5, 9.6 Hz), 8.17 (d, 1 H, J=5.6 Hz); MS (ESI$^+$) m/z 448.01 (M+H)$^+$.

Preparation 3D: 4-(4-Amino-2-fluorophenoxy)-3-chloro-N-(diphenylmethylene) pyridin-2-amine

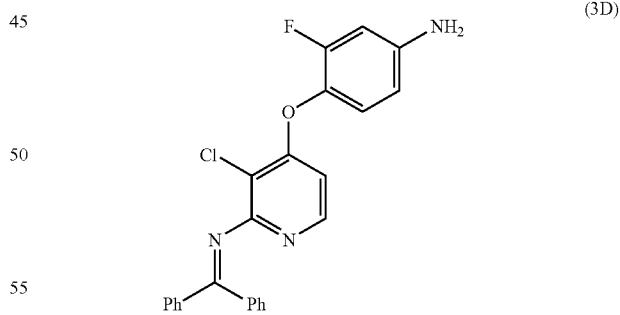

(3D)

The following materials were added to a 2-L Chem-Glass reactor: 3-chloro-N -(diphenylmethylene)-4-(2-fluoro-4-nitrophenoxy)pyridin-2-amine (110.00 g, 221 mmol), isopropyl alcohol (990.00 mL), and ammonium sulfide (~40% in water, 297.00 mL, 2324 mmol). The mixture was allowed to stir at 20° C. for 3-4 h. 3-Chloro-N -(diphenylmethylene)-4-(2-fluoro-4-nitrophenoxy)pyridin-2-amine was not detected by HPLC analysis. The reaction mixture was heated to 70° C. and allowed to stir for 3-4 h. Once the reaction was complete, water (14 mL/g·LR) was added. The reaction mixture was cooled to 20° C. (reaction temp) over 1 h. Upon cooling a solid precipitated and was filtered off and washed with water (12.5 mL/g·LR), followed by heptane:MTBE (4:1; 5 mL/g·LR). After LOD (~25%), 95.3 g of crude 4-(4-amino-2-fluorophenoxy)-3-chloro-N-(diphenylmethylene)pyridin-2-amine (90AP) was obtained. The crude 4-(4-amino-2-fluorophenoxy)-3-chloro-N-(diphenylmethylene)pyridin-2-amine was dissolved into n-BuOAc (7 mL/g·LR) by heating to approximately 85° C. At 85° C., heptane (7 mL/g·LR) was added dropwise until the solution became cloudy. The solution was then allowed to cool to 20° C. with stirring. Once at 20° C., the slurry was aged for 8 h. The solid was filtered, washed with heptane (5 mL/g·LR), and then dried overnight in a vacuum oven at 60° C. to afford 4-(4-amino-2-fluorophenoxy)-3-chloro-N-(diphenylmethylene)pyridin-2-amine (62.53 g; 67.69% yield) as a faint yellow solid. $^1$H NMR (CDCl$_3$) δ 6.23 (dd, 1 H, J=1.0, 5.6 Hz), 6.43 (m, 1 H), 6.49 (dd, 1 H, J=2.5, 12.1 Hz), 6.92 (t, 1 H, J=8.6 Hz), 7.25-7.60 (m, 8 H), 7.87 (m, 2 H), 7.95 (d, 1 H, J=6.1 Hz); MS (ESI$^+$) m/z 418.6 (M+H)$^+$.

Preparation 3E: Ethyl 4-(4-fluorophenyl)-3-oxobutanoate

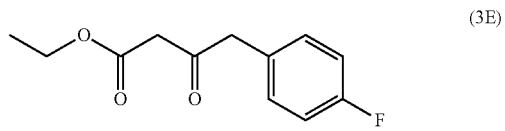 [SMILES: CCOC(=O)CC(=O)Cc1ccc(F)cc1]

(3E)

To a solution of 2,2-dimethyl-1,3-dioxane-4,6-dione (Meldrum's acid, 8.0 g, 56 mmol) dissolved in anhydrous methylene chloride (100 mL) and pyridine (11 mL), at 0° C. under nitrogen atmosphere, was slowly added 2-(4-fluorophenyl)acetyl chloride (7.6 mL, 9.6 g, 56 mmol). The red solution was stirred at 0° C. for 1.5 h. The reaction mixture was treated with 1 N HCl (13 mL) and diluted with methylene chloride (200 mL). The layers were separated and the organic layer was washed with saturated aqueous sodium chloride, dried and concentrated in vacuo to give 5-(2-(4-fluorophenyl)acetyl)-2,2-dimethyl-1,3-dioxane-4,6-dione. The crude intermediate was suspended in absolute EtOH (150 mL) and the resulting mixture was refluxed for 4 hours. The solvent was then removed in vacuo and the residue was purified by flash column chromatography (SiO2, 230-400 mesh, 8:1 hexane-ethyl acetate gradient elution) to afford the desired product (4.6 g, 37%). 1H NMR (CDCl$_3$) δ 7.23-7.15 (m, 2 H), 7.05-6.98 (m, 2 H), 4.18 (q, 2 H, J=7.0 Hz), 3.81 (s, 2 H), 3.46 (s, 2 H), 1.26 (t, 3 H, J=7.0 Hz); MS (ESI+) m/z 225 (M+H)$^+$.

Preparation 3F: 5-(4-Fluorophenyl)-4-oxo-1,4-dihydropyridine-3-carboxylic acid

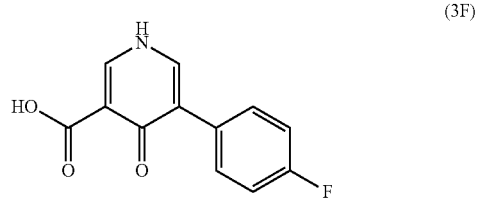 [SMILES: O=C(O)c1c[nH]cc(-c2ccc(F)cc2)c1=O]

(3F)

To a solution of ethyl 4-(4-fluorophenyl)-3-oxobutanoate (4.6 g, 21 mmol) in absolute EtOH (45 mL) was added NaOEt solution (21% NaOEt solution in EtOH, 7.7 mL) and triazine (1.67 g, 21 mmol). The resulting mixture was heated to 85° C. for 1.5 h, cooled to room temperature and treated with an additional portion of triazine (0.08 g, 1 mmol) and NaOEt solution (21% NaOEt solution in EtOH, 0.4 mL). The reaction mixture was heated for an additional hour and concentrated in vacuo. The residue was treated with 1N HCl until the pH of the reaction was about 2. The precipitate was collected to give the desired ester intermediate, ethyl 5-(4-fluorophenyl)-4-oxo-1,4-dihydropyridine-3-carboxylate (4.5 g, 83%) as a yellow solid. MS (ESI$^+$) m/z 262 (M+H)$^+$.

The above ester (1.0 g, 3.8 mmol) was dissolved in 2N NaOH (20 mL) and heated to 65° C. for 2 h. The resulting clear mixture was cooled to ambient temperature and the solids were filtered off. The filtrate was then acidified with 1N HCl to pH=1 and the resulting yellow precipitate was collected as the desired product (0.73 g, 82%). $^1$H NMR (DMSO-d$_6$) δ 13.52 (br s, 1 H), 8.86 (s, 1 H), 8.51 (s, 1 H), 7.99-7.96 (m, 2 H), 7.55-7.51 (m, 2 H); MS (ESI$^+$) m/z 234 (M+H)$^+$.

Preparation 3G: N-(4-(3-Chloro-2-(diphenylmethyleneamino)pyridin-4-yloxy)-3-fluorophenyl)-5-(4-fluorophenyl)-4-oxo-1,4-dihydropyridine-3-carboxamide

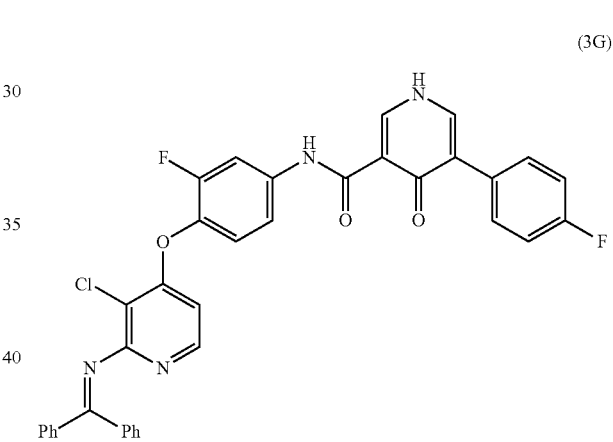

(3G)

To a solution of 4-(4-amino-2-fluorophenoxy)-3-chloro-N-(diphenylmethylene) pyridin-2-amine (836 mg, 2.0 mmol) and 5-(4-fluorophenyl)-4-oxo-1,4-dihydropyridine-3-carboxylic acid (490 mg, 2.0 mmol) in DMF (10 mL) at room temperature were added HATU (913 mg, 2.4 mmol) and DIPEA (1.05 ml, 6.0 mmol). The reaction mixture was stirred at room temperature for 3 h prior to being quenched by the addition of cold water (50 mL). The solid that formed was collected by filtration, and washed with water and ether. The solid was dissolved in DCM and purified by flash column chromatography (SiO$_2$, DCM to 10% MeOH in DCM) to give the desired product (987 mg, 78%) as a light yellow solid. MS (ESI) m/z 633 (M+H)$^+$.

Example 3

To a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (410 mg, 0.65 mmol) in THF (10 mL) at room temperature was added aqueous HCl (2 M, 0.81 mL, 1.62 mmol). The reaction mixture was stirred at room temperature for 1 h and then concentrated in vacuo. Cold 5% aq. NaHCO$_3$ (5 mL) was then added to the residue. The solid that formed was collected by filtration, washed with water and then ether, and dried under vacuum to give the desired product (275 mg, 90%). $^1$H NMR (DMSO-d$_6$) δ 13.31 (s, 1 H), 12.70 (br s, 1 H), 8.63 (d, 1 H, J=1.30 Hz), 8.09 (d, 1 H, J=1.50 Hz), 8.02 (dd, 1 H, J=2.50, 13.10 Hz), 7.76 (d, 1 H, J=5.50 Hz), 7.71 (m, 2 H), 7.44 (dd, 1 H, J=1.50, 8.80 Hz), 7.31 (t, 1 H, J=8.80 Hz), 7.27 (t, 2H, J=8.80 Hz), 6.43 (br s, 2 H), 5.96 (d, 1 H, J=5.60 Hz); MS (ESI$^+$) m/z 469 (M+H)$^+$.

N-(4-(2-Amino-3-chloropyridin-4-yloxy)-3-fluorophenyl)-5-(4-fluorophenyl)-4-oxo-1,4-dihydropyridine-3-carboxamide, hydrochloride salt The HCl salt of N-(4-(2-amino-3-chloropyridin-4-yloxy)-3-fluorophenyl)-5-(4-fluorophenyl)-4-oxo-1,4-dihydropyridine-3-carboxamide (Example 3) is obtained by treating a solution of N-(4-(3-chloro-2-(diphenylmethyleneamino)pyridin-4-yloxy)-3-fluorophenyl)-5-(4-fluorophenyl)-4-oxo-1,4-dihydropyridine-3-carboxamide (Preparation 3G) in THF with excess aqueous HCl at room temperature. The volatiles are removed in vacuo to provide the desired compound.

Example 4

Alternative Synthesis of 3-Chloro-N-(diphenylmethylene)-4-(2-fluoro-4-nitrophenoxy) pyridin-2-amine Preparation 4A: 2,3-dichloropyridin-4-ol

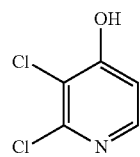

(4A)

A first solution was prepared by dissolving 2.3-Dichloropyridine (100 g, 0.68 mol) and triisopropyl borate (315 mL, 1.37 mol) in THF (150 mL). The resulting solution was cooled to −10° C. In a separate reactor, a second solution was prepared by dissolving diisopropylamine (150 mL, 1.07 mol) in THF (500 mL). The second solution was cooled to −10° C. and under nitrogen, n-butyl lithium (420 mL, 1.05 mol) was added over 20 min. After stirring for 10 min, the second solution was added slowly to the first solution via vacuum transfer.

The reaction mixture was stirred for 3 hrs at 22° C. until HPLC analysis indicated reaction completion. Water (1.00 L) was added to the mixture, followed by addition of sodium percarbonate (238 g) in two portions. The resulting mixture was allowed to stir at 20° C. for 1 h. The pH of the mixture was adjusted to pH 2-3 by addition of conc. HCl (300 mL). Next, solid NaHSO$_3$ (85 g) was added. The aqueous layer was separated and extracted with toluene (150 mL). The combined organic layers were washed with water (two times 100 mL) and concentrated by atmospheric distillation (distillation temperature up to 90° C.) to about 500 mL. The resulting slurry was cooled to 20° C. and filtered on a Buechner funnel. The cake was washed with heptane (two times 100 mL) and subsequently dried to yield 100.9 g (91%) of 2,3-dichloropyridin-4-ol as white solid.

Preparation 4B:
2,3-dichloro-4-(2-fluoro-4-nitrophenoxy)pyridine

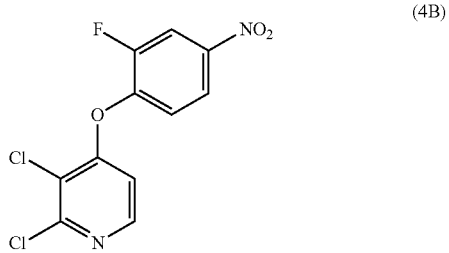 [SMILES: O=[N+]([O-])c1ccc(Oc2ccnc(Cl)c2Cl)c(F)c1]

(4B)

To a 2-L Chem-Glass reactor was added 2,3-dichloropyridinol (90 g, 0.55 mol), 3,4-difluoronitrobenzne (100 g, 0.63 mol), lithium carbonate (59.4 g, 0.80 mol) and dimethyl sulfoxide (360 mL). The mixture was heated to 115° C. for 21 hrs, until the reaction was deemed complete by HPLC analysis. The mixture was cooled to 25° C. and methanol (180 mL) was added, followed by water (960 mL). The mixture was neutralized by addition of conc. HCl (60 g) and the resulting slurry was stirred at 35° C. for 1 h. After cooling to 28° C., the slurry was filtered on a Buechner funnel and the filter cake was washed with water (four times 250 mL). The crude cake was then suspended in methanol (20 mL) and water (250 mL), and the resulting mixture was stirred for 20 min at 45° C. After cooling to 25° C., the slurry was filtered. The resulting cake washed with heptane (two times 75 mL) and dried under vacuum to yield 164.68 g (99%) of 2,3-dichloro-4-(2-fluoro-4-nitrophenoxy)pyridine as yellow solid.

Preparation 4C: 3-Chloro-N-(diphenylmethylene)-4-(2-fluoro-4-nitrophenoxy) pyridin-2-amine

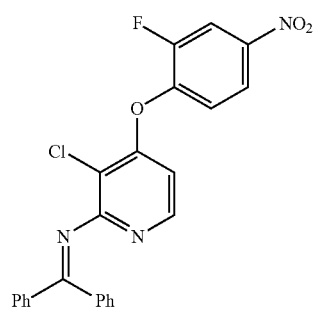

(4C)

To a 2.5-L Chem-Glass reactor was added 2,3-dichloro-4-(2-fluoro-4-nitrophenoxy) pyridine (50 g, 0.165 mol), benzoimine (30 g, 0.165 mol), cesium carbonate (110 g, 0.321 mol), palladium acetate (0.9 g, 4.0 mmol), racemic 2,2'-bis(diphenylphosphino)1,1'-binaphthyl (3.25 g, 5.1 mmol), and xylene (300 mL). The mixture was heated to 125° C. for 11 hrs. The mixture was cooled to 50° C. and silicagel (20 g) and xylene (300 mL) were added. The suspension was stirred for 30 min at 50-55° C. and filtered on a Buechner funnel. The filter cake was washed with xylene (two times 100 mL). The filtrates were combined, washed with water (two times 150 mL) and concentrated to about 150 mL by distillation on a rotary evaporator. After cooling to 25° C., heptane (300 mL) was added to the mixture. The resulting slurry was stirred at 25° C. for 16 hrs. Additional heptane (150 mL) was added to the slurry and the slurry was filtered on a Buechner funnel. The cake was washed with a mixture of xylene 1:10 heptane (100 mL), followed by n-heptane (two times 100 mL). After drying under vacuum, 47.41 g (64%) of 3-Chloro-N-(diphenylmethylene)-4-(2-fluoro-4-nitrophenoxy) pyridin-2-amine was obtained. $^1$H NMR (CDCl$_3$) δ; MS (ESI$^+$) m/z (M+H)$^+$

What is claimed is:

1. A compound having the structure:

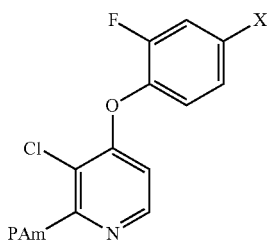

or a salt thereof, wherein:
X is NO$_2$ or NH$_2$; and
PAm is —NH—R$^b$, —NHC(O)OR$^a$, —NHC(=O)R$^a$, —NH(CH$_2$R$^c$), —NHSi(R$^d$)$_3$, —NH(PO(OR$^d$)$_2$, —NHSO$_2$R$^e$, —N(R$^b$)$_2$, —N(C(O)OR$^a$)$_2$, —N(C(O)R$^a$)$_2$, —N(CH$_2$R$^c$)$_2$, —N(Si(R$^d$)$_3$), —N=C(R$^a$)$_2$, or

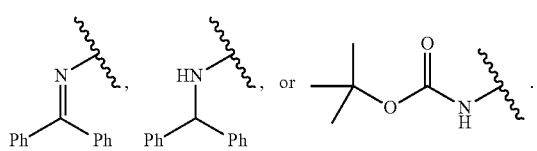

each R$^a$ is independently H, alkyl, haloalkyl, benzyl, or aryl;
each R$^b$ is independently alkyl, haloalkyl, benzyl, methoxybenzyl, or aryl;
each R$^c$ is independently allyl or alkoxy;
each R$^d$ is independently alkyl;
R$^e$ is alkyl, alkyl substituted with —Si(alkyl)$_3$, phenyl, or nitrophenyl; and
each R$^f$ is independently alkyl or benzyl.

2. The compound according to claim 1, or a salt thereof, wherein:
PAm is

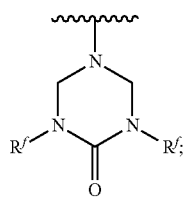

3. The compound according to claim 1, or a salt thereof, wherein:
PAm is

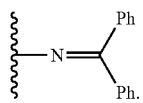

4. The compound according to claim 1, or a salt thereof, wherein:
X is NO$_2$.

5. The compound according to claim 1, or a salt thereof, wherein:
X is NO$_2$; and
PAm is

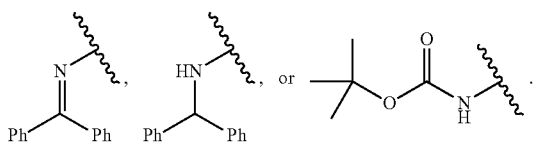

6. The compound according to claim 1, or a salt thereof, wherein:
X is NO$_2$; and
PAm is

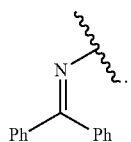

7. The compound according to claim 1, or a salt thereof, wherein:
X is NH$_2$.

8. The compound according to claim 1, or a salt thereof, wherein:
X is NH$_2$; and
PAm is

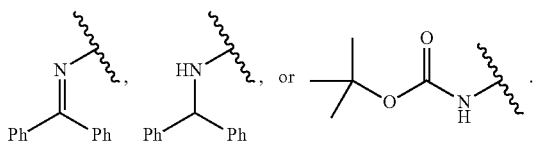

9. The compound according to claim 1, or a salt thereof, wherein:
X is NH$_2$; and
PAm is

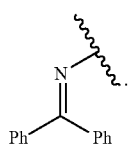

* * * * *